US008287853B2

(12) United States Patent
Cool et al.

(10) Patent No.: US 8,287,853 B2
(45) Date of Patent: *Oct. 16, 2012

(54) METHODS OF CULTURING MESENCHYMAL STEM CELLS

(75) Inventors: Simon McKenzie Cool, Singapore (SG); Victor Nurcombe, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1104 days.

This patent is subject to a terminal disclaimer.

(21) Appl. No.: 12/189,013

(22) Filed: Aug. 8, 2008

(65) Prior Publication Data
US 2009/0148420 A1    Jun. 11, 2009

Related U.S. Application Data

(63) Continuation-in-part of application No. 11/816,153, filed as application No. PCT/IB2006/000278 on Feb. 13, 2006, now Pat. No. 8,178,085.

(60) Provisional application No. 60/651,633, filed on Feb. 11, 2005, provisional application No. 61/082,436, filed on Jul. 21, 2008.

(51) Int. Cl.
A01N 63/00    (2006.01)
A01N 1/02    (2006.01)
C12N 5/00    (2006.01)

(52) U.S. Cl. .......... 424/93.1; 424/93.7; 435/2; 435/325; 435/343

(58) Field of Classification Search ............... 424/93.1, 424/93.7; 435/2, 325, 343
See application file for complete search history.

(56) References Cited

U.S. PATENT DOCUMENTS

| 5,605,829 | A | 2/1997 | McGlave et al. |
| 5,980,885 | A | 11/1999 | Weiss et al. |
| 6,071,889 | A | 6/2000 | Weiss et al. |
| 2007/0116680 | A1 | 5/2007 | Stegemann et al. |
| 2009/0137038 | A1 | 5/2009 | Nurcombe et al. ........... 436/366 |
| 2009/0148422 | A1 | 6/2009 | Nurcombe et al. .......... 424/93.7 |

FOREIGN PATENT DOCUMENTS

| EP | 1 857 545 A1 | 11/2007 |
| WO | 9615226 A1 | 5/1996 |
| WO | 9623003 A1 | 8/1996 |
| WO | 9920741 A1 | 4/1999 |
| WO | WO 2004/085630 A1 | 10/2004 |
| WO | 2006085209 A1 | 8/2006 |

OTHER PUBLICATIONS

Hou et al., Induction of umbilical cord blood mesenchymal stem cells into neuron-like cells in vitro Int J Hematol. Oct. 2003;78(3):256-61.*
Solchaga et al., FGF-2 enhances the mitotic and chondrogenic potentials of human adult bone marrow-derived mesenchymal stem cells. J Cell Physiol. May 2005;203(2):398-409.*
Simmons et al Blood. Dec. 1, 1991;78(11):2848-53.CD34 expression by stromal precursors in normal human adult bone marrow.*
Gronthos et al Molecular and cellular characterisation of highly purified stromal stem cells derived from human bone marrow Journal of Cell Science 116, 1827-1835.*
Brickman et al., "Structural comparison of fibroblast growth factor-specific heparan sulfates derived from a growing or differentiating neuroepithelial cell line" Glycobiology 8(5): 463-471, 1998.
Brickman et al., "Structural Modification of Fibroblast Growth Factor-binding Heparan Sulfate at a Determinative Stage of Neural Development" The Journal of Biological Chemistry 273(8): 4350-4359, Feb. 20, 1998.
Chipperfield et al., "Heparan sulfates isolated from adult neural progenitor cells can direct phenotypic maturation" Int. J. Dev. Biol. 46: 661-670, 2002.
Colter et al., "Rapid expansion of recycling stem cells in cultures of plastic-adherent cells from human bone marrow" PNAS 97(7): 3213-3218, Mar. 28, 2000.
Cool et al., "Heparan Sulfate Regulation of Progenitor Cell Fate" Journal of Cellular Biochemistry 99: 1040-1051, 2006.
Haik et al., "Fibroblast growth factor 2 up regulates telomerase activity in neural precursor cells" Oncogene 19: 2957-2966, 2000.
Hienola et al., "HB-GAM inhibits proliferation and enhances differentiation of neural stem cells" Molecular and Cellular Neuroscience 26: 75-88, 2004.
Jorgensen et al., "Tissue engineering through autologous mesenchymal stem cells" Current Opinion in Biotechnology 15: 406-410, 2004.
Lindahl et al., "Regulated Diversity of Heparan Sulfate" The Journal of Biological Chemistry 273(39): 24979-24982, Sep. 25, 1998.
Luong-Van et al., "The in vivo assessment of a novel scaffold containing heparan sulfate for tissue engineering with human mesenchymal stem cells" J. Mol. Hist. 38: 459-468, 2007.
Nurcombe et al., "Developmental Regulation of Neural Response to FGF-1 and FGF-2 by Heparan Sulfate Proteoglycan" Science 260, 103-106, Apr. 2, 1993.
Nurcombe et al., "The Proliferative and Migratory Activities of Breast Cancer Cells Can Be Differentially Regulated by Heparan Sulfates" The Journal of Biological Chemistry 275(39): 30009-30018, Sep. 29, 2000.
Shi et al., "Bone formation by human postnatal bone marrow stromal stem cells is enhanced by telomerase expression" Nature Biotechnology 20: 587-591, Jun. 2002.
Simonsen et al., "Telomerase expression extends the proliferative life-span and maintains the osteogenic potential of human bone marrow stromal cells" Nature Biotechnology 20: 592-596, Jun. 2002.
Sugahara et al., "Recent advances in the study of the biosynthesis and functions of sulfated glycosaminoglycans" Current Opinion in Structural Biology 10: 518-527, 2000.
Yudoh et al., "Reconstituting Telomerase Activity Using the Telomerase Catalytic Subunit Prevents the Telomere Shorting and Replicative Senescence in Human Osteoblasts" Journal of Bone and Mineral Research 16: 1453-1464, 2001.

(Continued)

*Primary Examiner* — Maria Leavitt
(74) *Attorney, Agent, or Firm* — Seed IP Law Group PLLC

(57) ABSTRACT

Stem cells obtained through in vitro culture with heparan sulphate are described.

1 Claim, 25 Drawing Sheets

OTHER PUBLICATIONS

Bartlett et al., "Regulation of neural stem cell differentiation in the forebrain," *Immunology and Cell Biology* 76:414-418, 1998.

Brickman et al., "Heparan Sulfates Mediate the Binding of Basic Fibroblast Growth Factor to a Specific Receptor on Neural Precursor Cells," *The Journal of Biological Chemistry* 270(42):24941-24948, 1995.

Matsubara et al., "A new technique to expand human mesenchymal stem cells using basement membrane extracellular matrix," *Biochemical and Biophysical Research Communications* 313:503-508, 2004.

Ng et al., "Osteogenic Differentiation of Murine Embryonic Stem Cells Is Mediated by Fibroblast Growth Factor Receptors," *Stem Cells and Development* 16:305-318, 2007.

Office Action for U.S. Appl. No. 12/329,460, mailed Sep. 27, 2010, 34 pages.

Office Action for U.S. Appl. No. 11/816,153, mailed Sep. 27, 2010, 25 pages.

Engler et al., "Matrix Elasticity Directs Stem Cell Lineage Specification," *Cell* 126:677-689, 2006.

Lee et al., "In Vitro Hepatic Differentiation of Human Mesenchymal Stem Cells," *Hepatology* 40:1275-1284, 2004.

Nurcombe et al., "Methods of Proliferating Stem Cells," Office Action mailed May 24, 2011, for U.S. Appl. No. 12/329,460, 14 pages.

Nurcombe et al., "Methods of Proliferating Stem Cells," Office Action mailed May 20, 2011, for U.S. Appl. No. 11/816,153, 15 pages.

* cited by examiner

| CONDITION | E 10 |
|---|---|
| pronase | 40,000 |
| mild alkali treatment | 25,000 |
| heparinase | 7,000 |
| number of heparinase resistant domains | 2 |

| | % E 10 |
|---|---|
| TREATMENT | |
| Heparitinase | 61.5 |
| Heparinase | 15.3 |
| HNO$_2$ | 49.0 |

Figure 15

| | %E10 GAG |
|---|---|
| DISACCHARIDE | |
| IdoA/GlcA-AMann$_R$ | 12.9 |
| IdoA(2S)-AMann$_R$ | 53.4 |
| GlcA-AMann$_R$(6S) | 10.25 |
| IdoA-AMann$_R$(6S) | 3.4 |
| IdoA(2S)-AMann$_R$(6S) | 18.7 |
| GlcA(2S)-AMann$_R$ | 1.0 |
| GlcA-AMann$_R$(3S) | 0.30 |
| GlcA-AMann$_R$(3,6S) | 0.15 |
| UNKNOWN | 0.0 |

Figure 16

| | % IN E10 |
|---|---|
| sulfation number : peak number | |
| Non-sulfated : 1 | 37.2 |
| Mono-sulfated : 1 | 1.5 |
| Mono-sulfated : 2 | 1.0 |
| Mono-sulfated : 3 | 0.3 |
| Mono-sulfated : 4 | 0.3 |
| Mono-sulfated : 5 | 7.7 |
| Mono-sulfated : 6 | 23.9 |
| Mono-sulfated : 7 | 18.4 |
| Mono-sulfated : 8 | 0.7 |
| Mono-sulfated : 9 | 0.4 |
| Di-sulfated : 1 | 1.8 |
| Di-sulfated : 2 | 0.9 |
| Di-sulfated : 3 | 2.7 |
| Di-sulfated : 4 | 1.5 |
| Tri-sulfated : 1 | 1.0 |
| Tri-sulfated : 2 | 0.0 |
| Tri-sulfated : 3 | 0.3 |
| Tri-sulfated : 4 | 0.4 |
| TOTAL | 100 |

Figure 17

| PEAK NUMBER | DISACCHARIDE | % in E10 GAG |
| --- | --- | --- |
| 1 | ΔHexUA-GlcNAc | 44.8 |
| 3 | ΔHexUA-GlcNSO$_3$ | 21.5 |
| 2 | ΔHexUA-GlcNAc(6S) | 8.0 |
| 7 | ΔHexUA(2S)-GlcNAc | 2.4 |
| 4 | ΔHexUA-GlcNSO$_3$(6S) | 4.0 |
| 5 | ΔHexUA(2S)-GlcNSO$_3$ | 12.4 |
| 8 | ΔHexUA(2S)-GlcNAc(6S) | 0.2 |
| 6 | ΔHexUA(2S)-GlcNSO$_3$(6S) | 4.1 |
| 9 | unknown | 2.4 |

Figure 18

| SULFATION | % in E10 GAG |
|---|---|
| Total sulfation/100 disaccharides | 77.4 |
| 6-O-Sulfate | 16.3 |
| 2-O-Sulfate | 19.1 |
| N-Sulfate | 42.0 |
| O-Sulfate | 35.4 |
| ratios of sulfations | |
| 2-O-Sulfate/6-O-Sulfate | 1.17 |
| N-Sulfate/O-Sulfate | 1.19 |
| N-Sulfate/2-O-Sulfate | 2.2 |
| N-Sulfate/6-Sulfate | 2.58 |

Figure 19

A)
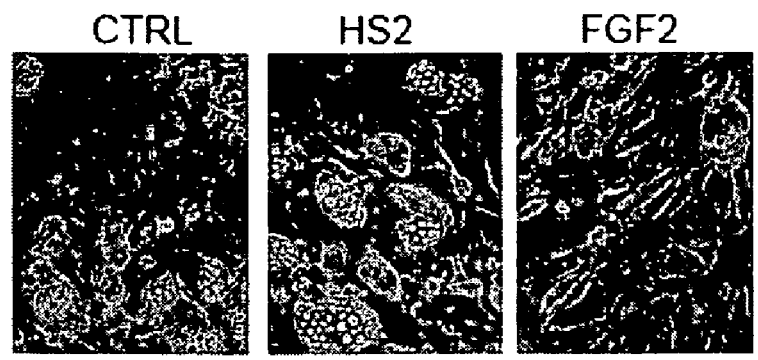
B)
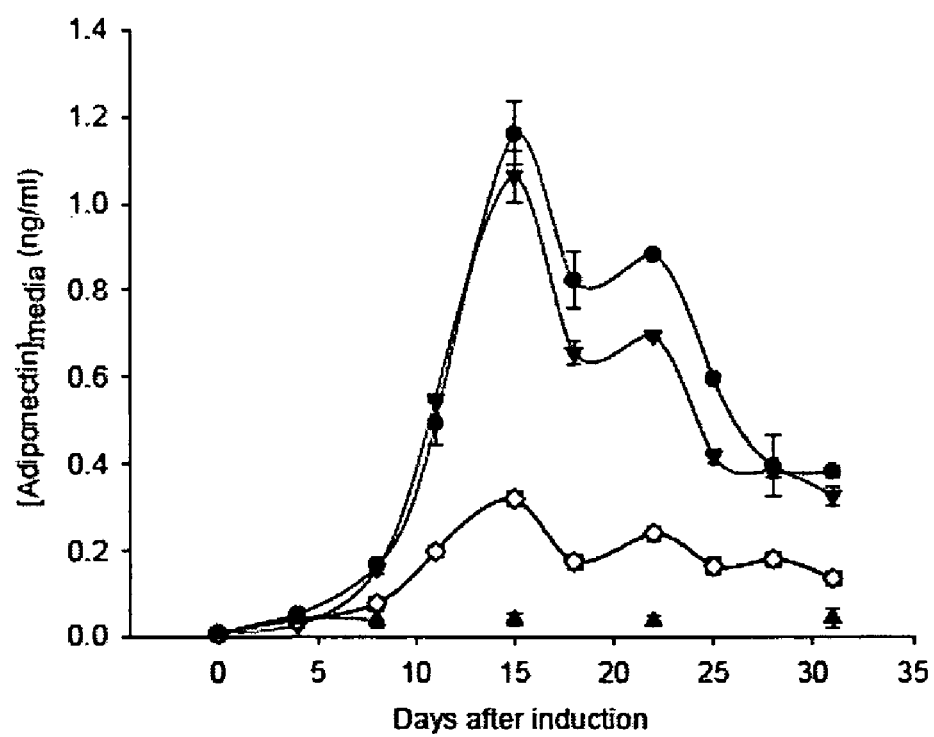
Figure 24

A)
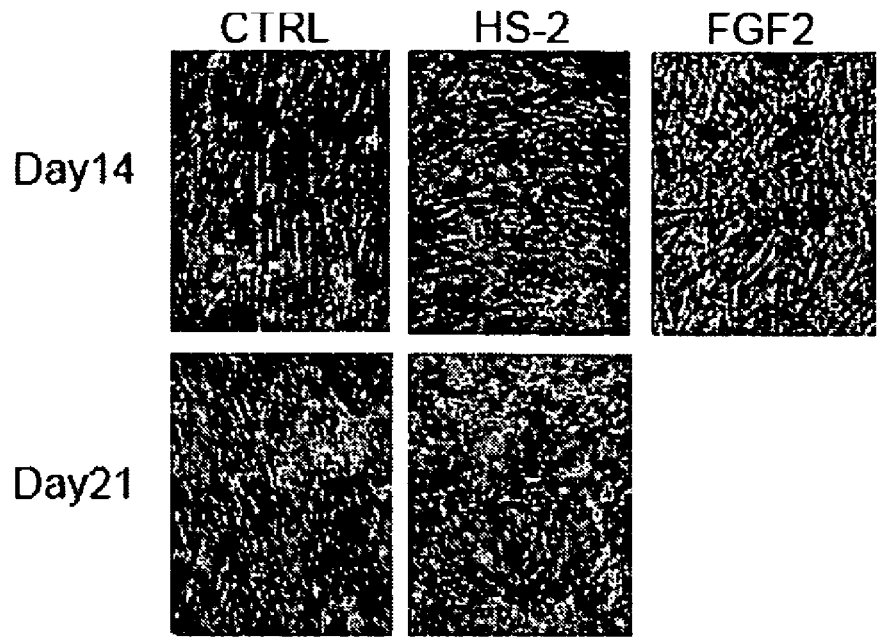
B)
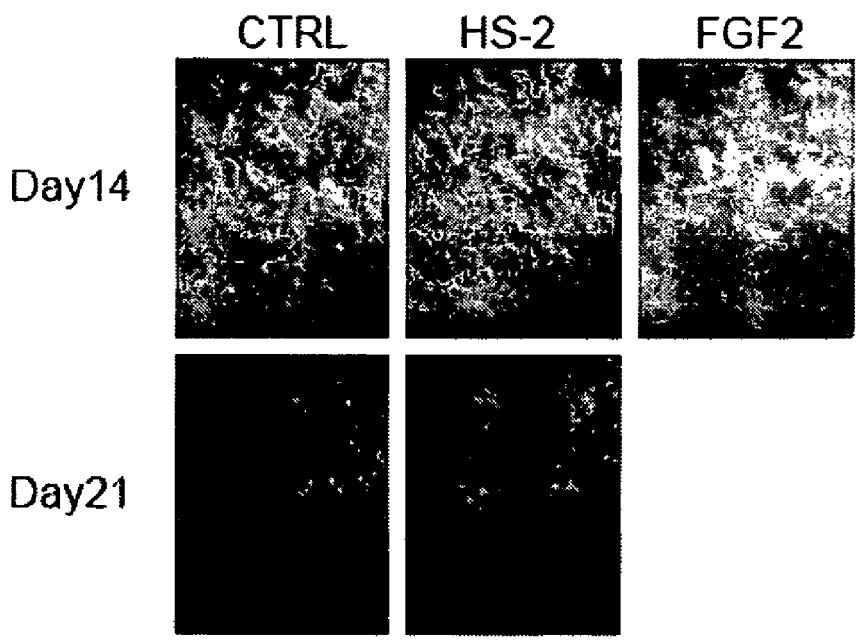
Figure 25

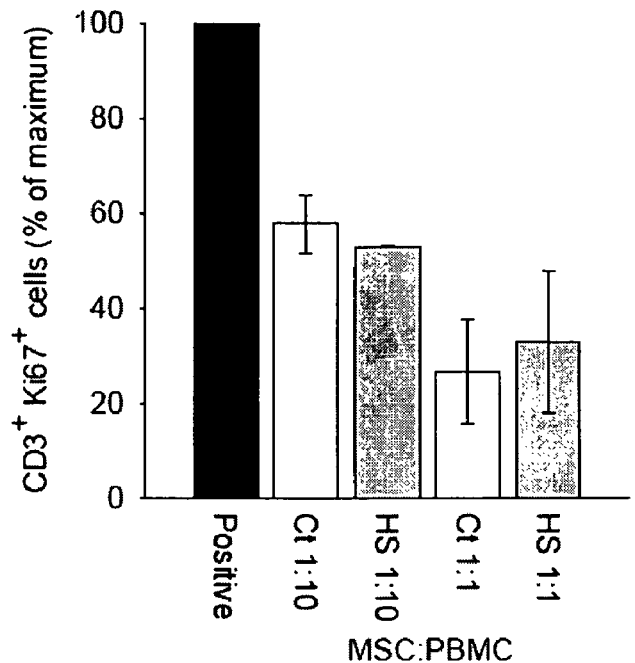

Figure 26

| Gene | Primers | Probe | ACC number |
|---|---|---|---|
| 18S | F: TTCGAGGCCCTGTAATTGGA | AGTCCACTTTAAATCCTT | AY248756 |
| | R: GCAGCAACTTTAATATACGCTATTGG | | |
| AlkPhos | F: ATGCCCTGGAGCTTCAGAAG | acgtTGgCtAaGaAtGtCaTc | NM_000478 |
| | R: TGGTGGAGCTGACCCTTGAG | | |
| BSPII | F: AGAGGAAGCAATCACCAAAATGA | ctgCtTTaaTtTtgCtCagc | NM_004967 |
| | R: TTGAGAAAGCACAGGCCATTC | | |
| ALBP | F: GGAAAGTCAAGAGCACCATAACCT | aaatCaAcCaCcaTaAaGaGa | BC003672.1 |
| | R: TTCCACCACCAGTTTATCATCCT | | |
| C/EBPα | F: GAGGGACCGGAGTTATGACAAG | aataTtTtGcTtTatCaGcCgat | NM_004364.2 |
| | R: GGCACAGAGGCCAGATACAAG | | |
| Coll2a | F: GTACTTTCCAATCTCAGTCACTCTAGGA | ccCcTCtCTttCTaAgaga | NM_033150 |
| | R: TTTTATTTTGCAGTCTGCCCAGTT | | |
| SOX9 | F: AAAGGCAACTCGTACCCAAATTT | caAgaCaCaAaCAtgAcc | Z46629 |
| | R: AGTGGGTAATGCGCTTGGAT | | |

Figure 27

| Table S2 | No. | Unigene | RefSeq # | Symbol | Description |
|---|---|---|---|---|---|
| Cluster 1 | 1 | Hs.522891 | NM_000609 | CXCL12 | Chemokine (C-X-C motif) ligand 12 (stromal cell-derived factor 1) |
| | 2 | Hs.471119 | NM_001204 | BMPR2 | Bone morphogenetic protein receptor, type II (serine/threonine kinase) |
| | 3 | Hs.453951 | NM_013957 | NRG1 | Neuregulin 1 |
| | 4 | Hs.429052 | NM_002211 | ITGB1 | Integrin, beta 1 (fibronectin receptor, beta polypeptide, antigen CD29 includes MDF2, MSK12) |
| | 5 | Hs.420269 | NM_001849 | COL6A2 | Collagen, type VI, alpha 2 |
| | 6 | Hs.369849 | NM_002392 | MDM2 | Mdm2, transformed 3T3 cell double minute 2, p53 binding protein (mouse) |

Figure 30

| Table S2 | No. | Unigene | RefSeq # | Symbol | Description |
|---|---|---|---|---|---|
| Cluster 1 | 7 | Hs.470316 | NM_001105 | ACVR1 | Activin A receptor, type I |
| | 8 | Hs.513609 | NM_005611 | RBL2 | Retinoblastoma-like 2 (p130) |
| | 9 | Hs.74615 | NM_006206 | PDGFRA | Platelet-derived growth factor receptor, alpha polypeptide |
| | 10 | Hs.502328 | NM_000610 | CD44 | CD44 antigen (homing function and Indian blood group system) |
| | 11 | Hs.28792 | NM_002192 | INHBA | Inhibin, beta A (activin A, activin AB alpha polypeptide) |
| | 12 | Hs.500483 | NM_001613 | ACTA2 | Actin, alpha 2, smooth muscle, aorta |
| | 13 | Hs.467824 | NM_015317 | PUM2 | Pumilio homolog 2 (Drosophila) |
| | 14 | Hs.436873 | NM_002210 | ITGAV | Integrin, alpha V (vitronectin receptor, alpha polypeptide, antigen CD51) |
| | 15 | Hs.532082 | NM_002184 | IL6ST | Interleukin 6 signal transducer (gp130, oncostatin M receptor) |
| | 16 | Hs.516105 | NM_001615 | ACTG2 | Actin, gamma 2, smooth muscle, enteric |
| Cluster 2 | 17 | Hs.95577 | NM_000075 | CDK4 | Cyclin-dependent kinase 4 |
| | 18 | Hs.201671 | NM_005686 | SOX13 | SRY (sex determining region Y)-box 13 |
| | 19 | Hs.521461 | NM_006158 | NEFL | Neurofilament, light polypeptide 68kDa |
| | 20 | Hs.238990 | NM_004064 | CDKN1B | Cyclin-dependent kinase inhibitor 1B (p27, Kip1) |
| | 21 | Hs.73793 | NM_003376 | VEGF | Vascular endothelial growth factor |
| | 22 | Hs.244723 | NM_001238 | CCNE1 | Cyclin E1 |
| | 23 | Hs.512234 | NM_000600 | IL6 | Interleukin 6 (interferon, beta 2) |
| | 24 | Hs.527971 | NM_006617 | NES | Nestin |
| | 25 | Hs.376032 | NM_002607 | PDGFA | Platelet-derived growth factor alpha polypeptide |
| Cluster 3 | 26 | Hs.125331 | XM_291161 | Dppa5 | Similar to developmental pluripotency associated 5; embryonal stem cell specific gene 1 |
| | 27 | Hs.482390 | NM_003243 | TGFBR3 | Transforming growth factor, beta receptor III (betaglycan, 300kDa) |
| | 28 | Hs.37092 | NM_005247 | FGF3 | Fibroblast growth factor 3 (murine mammary tumor virus integration site (v-int-2) oncogene homolog) |
| | 29 | Hs.370414 | NM_018055 | NODAL | Nodal homolog (mouse) |
| | 30 | Hs.408528 | NM_000321 | RB1 | Retinoblastoma 1 (including osteosarcoma) |
| | 31 | Hs.46366 | NM_000614 | CNTF | Ciliary neurotrophic factor |
| | 32 | Hs.133421 | NM_002310 | LIFR | Leukemia inhibitory factor receptor |
| | 33 | Hs.95582 | NM_006942 | SOX15 | SRY (sex determining region Y)-box 15 |

Figure 31

| Table S3 | Estimate ($\hat{L}$)[a] | Lower CL[b] | Upper CL[c] |
|---|---|---|---|
| Ctrl-d45 vs Ctrl-d21 | 3.704 | 3.018 | 4.416 |
| Ctrl-d45 vs Ctrl-d21 | 5.373 | 4.976 | 5.744 |
| HS2-d21 vs Ctrl-d21 | 8.761 | 7.921 | 9.653 |
| HS2-d32 vs Ctrl-d21 | 1.57 | 1.28 | 1.844 |
| HS2-d45 vs Ctrl-d21 | 3.008 | 2.758 | 3.328 |

METHODS OF CULTURING MESENCHYMAL STEM CELLS

CROSS-REFERENCE TO RELATED APPLICATIONS

This application is a continuation-in-part of U.S. patent application Ser. No. 11/816,153, International filing date of Feb. 13, 2006; which application is a U.S. National Phase of International Application No. PCT/IB2006/000278, filed Feb. 13, 2006; which application claims the benefit under 35 U.S.C. §119(e) of U.S. Provisional Application No. 60/651,633, filed Feb. 11, 2005; this application also claims the benefit under 35 U.S.C. §119(e) of U.S. Provisional Application No. 61/082,436, filed Jul. 21, 2008, all which applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 100151_402C1_ SEQUENCE_ LISTING.txt. The text file is 5 KB, was created on Nov. 25, 2008 and is being submitted electronically via EFS-Web.

FIELD OF THE INVENTION

The present invention relates to stem cells obtained through in vitro culture with heparan sulphate.

BACKGROUND TO THE INVENTION

In all tissues of the body there is a sub-population of adult stem cells. These multipotent cells are recruited and activated to take part in tissue regeneration. Adult stem cells are a promising resource for therapy, but their numbers are very low and they need propagation in vitro to be of therapeutic use. When these cells are cultured ex-vivo it has proven difficult to recreate their natural microenvironment, which is thought to be a sum of signals from interactions with the extracellular matrix and neighboring cells and the hormonal status of the microenvironment. Therefore, regenerative therapies using adult stem cells are still hampered by the limited number of available cells and the fact that their expansion in vitro, necessary to attain therapeutic numbers, compromises their differentiation and proliferative potential.

Due to their capacity to form cartilage, bone, fat and other connective tissue, human mesenchymal stem cells (hMSCs) constitute an exciting prospect for cell-based therapy in regenerating diseased or injured tissues. These adult stem cells can be readily purified from a small volume of bone marrow aspirates, and expanded in vitro for a limited number of population doublings (PD) (=30) before they reach replicative senescence. It is likely that this growth arrest is linked to telomere shortening as over-expression of the catalytic subunit of the telomerase (hTERT) is sufficient to increase the life span to several hundred population doublings. These "telomerized" cells retain their ability to assume phenotypes of mesenchymal tissues, thus providing a useful tool for the study of hMSCs. However, it does not address the issue of attaining a therapeutic number of multipotent stem cells in culture without severely affecting their regenerative potential.

The spontaneous differentiation of stem cells in culture is a result of a change in the microenvironment from that normally found in the naive stem cell niche. As mentioned above, the stem cell niche is a sum of signals from interactions with specific components of the extracellular matrix (ECM) and neighboring cells, and the hormonal status of the microenvironment.

Thus, there exists a need for methods and media compositions that help to overcome the problems encountered in the expansion of ex vivo stem cell cultures.

The capacity of adult human stem cells for both self-renewal and directed differentiation is efficacious for cell-based therapy, with bone marrow-derived human mesenchymal stem cells (hMSCs) representing one of the few stem cell types currently in clinical trials[1]. Tissue regeneration has been reported after delivery of adult stem cells either locally or systemically[2-5]. Moreover, hMSCs have shown potential for cardiovascular regeneration[6] and are currently undergoing phase III clinical trials. These cells have also shown potent immunosuppressive effects in vivo[7], making them particularly suited to transplantation. Despite such promise, widespread use of hMSCs is hindered by their low abundance (<0.01% of bone marrow mononuclear cells, BMMNCs)[8]. Successful enrichment of hMSCs using the monoclonal antibody STRO-1[9] is possible, although to reach sufficient numbers for therapy these cells require further ex vivo expansion. Although some ex vivo expansion is possible, a loss of multipotentiality occurs within a relatively short period of time[10]. Conditions that mimic the bone marrow microenvironment and maximize hMSC proliferation without adversely affecting multipotentiality ("stemness") are therefore needed.

Several strategies have been developed for the ex vivo expansion of hMSCs, including the forced expression of hTERT (telomerase catalytic sub-unit)[11,12], the addition of soluble peptide mitogens[13-18], and the use of extracellular matrix (ECM) molecules[19-21]. When transduced with hTERT, hMSCs fail to senesce and can be cultured for more than 260 population doublings. However these cells become tumorigenic[22], making this strategy untenable. The addition of growth factors, particularly fibroblast growth factor-2 (FGF-2), has also been shown to increase hMSC expansion. However it also increases the proliferation of more differentiated cells[18]. Key elements of the ECM are also known to support stem cell self-renewal, and strategies that manipulate them have shown promise[20]. One of the most active ECM species contributing to improved growth is the family of heparan sulphate (also called heparan sulphate or HS) glycosaminoglycan (GAG) sugars[23,24]; the actions of many growth factors are known to be dependent on specific forms of this carbohydrate.

A major challenge for hMSC therapy is the provision of therapeutic numbers of multipotent stem cells. Current strategies utilized for generating hMSCs for clinical use rely on their isolation by adherence to plastic, followed by lengthy ex vivo expansion prior to re-implantation. However, many mesenchymal stem cells remain quiescent when isolated from adult bone marrow and cultured ex vivo, and will therefore fail to proliferate.

SUMMARY OF THE INVENTION

The inventors have now shown that heparan sulphate (HS) can be used to improve the culture of stem cells. When HS is contacted with stem cells, e.g. in the culture media, the stem cells exhibit a higher rate of cell proliferation and expansion of the stem cell culture occurs much faster. This enables larger quantities of multipotent stem cells to be obtained in a single culture having a much shorter culture period and without the need for further selection or separation of cells.

Not only can more stem cells be obtained but the stem cells obtained from culture with HS have improved properties, compared with stem cells obtained from culture in the absence of HS. In particular, stem cells from HS culture show a significant retention of stem cell properties compared to stem cells cultured in the absence of HS for the same period of time or for the same number of population doublings (PD). These stem cell properties may include longer telomere length, continued high level expression of molecular markers such as CD49a, CD73, CD105, CD90 and STRO-1 and maintenance of the multipotent properties of the stem cell, e.g. the ability to differentiate and form new tissue, and continued ability to minimise or avoid the host immune response.

HS culture therefore provides for the production of large quantities of multipotent stem cells that retain the core stem cell characteristics which give them great potential for use in methods of treatment of disease.

Stem cells cultured in HS have a unique genetic signature that is distinct from control cultures and can be objectively tested by analysis of gene expression and singular value decomposition. Stem cells cultured in HS show a much "younger" genetic signature compared to stem cells cultured in control culture (without HS) for the same length of time, i.e. the gene expression profile of stem cells cultured in HS is characteristic of cells grown in control cultures for a shorter period of time. This is consistent with the maintenance of stem cell multipotency when cultured in HS and the loss of multipotency and other stem cell characteristics in stem cells cultured in the absence of HS. Accordingly, stem cells cultured in HS represent a unique group of stem cells that are structurally distinguished from stem cells cultured in the absence of HS. Moreover, the provision of large volumes of these multipotent HS cultured stem cells (e.g. at levels of about $1\times10^4$-$1\times10^9$ cells), in a single culture of cells, is completely unique.

HS-2 has been shown to significantly increase the proliferation of a subpopulation of multipotent hMSCs that have significantly longer telomeres and a greater expression of cell surface antigens that are characteristic of hMSCs.

Methods according to the present invention are capable of yielding up to an 8-fold increase in available colony forming units. This is comparable to or better than current post-culture enrichment of stem cells, e.g. achieved by molecular cell sorting, for example sorting of human mesenchymal cells using STRO-1, carried out post-culture.

Accordingly, in one aspect of the present invention an in vitro culture of stem cells is provided, the culture comprising more than $1\times10^3$ multipotent stem cells.

In another aspect of the present invention a pharmaceutical composition is provided comprising more than $1\times10^3$ multipotent stem cells and a pharmaceutically acceptable carrier, adjuvant or diluent.

The stem cells are preferably obtained from, or obtainable from, culture in HS, more preferably in HS-2.

Preferably, the culture or pharmaceutical composition contains more than one of: $5\times10^3$, $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$ or $5\times10^9$ stem cells. The stem cells are preferably in contact with a heparan sulphate, which may be contained in the culture media or form part of the pharmaceutical composition. The culture media may contain other growth factors such as FGF-2. Preferably, the heparan sulphate is HS-2.

Preferably at least 3% of cells in the culture or composition are colony forming units (CFUs), more preferably one of at least 4%, 5%, 6%, 7%, 8% 9% or 10%. The percentage of CFUs provides a measure of the proportion of stem cells in a cell culture. Comparable levels of CFUs have not been obtained directly from cell culture before and previously post-culture selection and enrichment techniques have been required to select CFUs from the population of cultured cells.

The stem cells may have been cultured in HS, preferably HS-2, containing media for a minimum of 5 days. Culture in HS containing media may have been for a minimum of any one of: 7, 9, 11, 13, 15, 20, 25, 30, 35 or 40 days. Culture in HS containing media may have been for a maximum of any one of 7, 9, 11, 13, 15, 20, 25, 30, 35, 40, 45, 50 or more days.

The stem cells may express one or more of CD49a, CD73, CD105, CD90, STRO-1 and may optionally not express CD45. Preferably, the stem cells are adult mesenchymal stem cells wherein the stem cells are STRO-1$^{+bright}$.

In another aspect of the present invention an in vitro method of expanding a culture of stem cells is provided, the method comprising expanding a single stem cell to a population of more than $1\times10^3$ stem cells, the method comprising contacting a stem cell culture with HS-2.

The culture may initially contain more than one stem cell. The total expanded stem cell population is equivalent to the expansion of many single stem cells by more than $1\times10^3$. The degree of expansion may more preferably be one of: $5\times10^3$, $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$ or $5\times10^9$.

The culture time to expand the stem cells may be between 5 and 50 days, more preferably between 10 and 45 days and more preferably less than one of 45 days, 40 days, 35 days, 30 days, 25 days, 20 days or 15 days.

In a related aspect of the present invention an in vitro method of expanding a culture of stem cells is provided, the method comprising expanding a culture of stem cells from an initial culture size of at least about 2000 cells per cm$^2$ of culture space (e.g. of the culture dish or plastic) to an expanded culture size that contains at least $1\times10^3$ times more stem cells (i.e. at least about $2\times10^6$ stem cells), the method comprising contacting a stem cell culture with HS-2. More preferably the initial culture size is one of at least about 3,000 cells per cm$^2$, about 3500 cells per cm$^2$, at least about 4000 cells per cm$^2$, about 4500 cells per cm$^2$, 5000 cells per cm$^2$ and the expanded culture size is one of at least about $3\times10^6$ cells per cm$^2$, about $3.5\times10^6$ cells per cm$^2$, at least about $4\times10^6$ cells per cm$^2$, about $4.5\times10^6$ cells per cm$^2$, $5\times10^6$ cells per cm$^2$.

The initial culture may have less than one of: 6000, 5000, 4000, 3000 or 2000 cells per cm$^2$. The expanded culture may have more than one of: $5\times10^3$, $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$ or $5\times10^9$ stem cells.

The culture time to expand between the initial culture size and the expanded culture size is preferably between about 10 and 50 days, more preferably between about 15 and 30 days. It may be less than one of 50, 45, 40, 35, 30, 25, 20 or 15 days.

The method may be applied to expand the stem cell culture to an expanded culture size of $1\times10^4$, $1\times10^5$, $1\times10^6$, $1\times10^7$, $1\times10^8$, $1\times10^9$ cells or greater.

Cells used for cell culture may comprise stem cells, e.g. mesenchymal stem cells and may also comprise other cells, e.g. non-stem cells associated with the stem cells in the tissue from which the stem cells are collected, and/or supporting cells. Cells used to initiate a culture of stem cells will preferably contain a high proportion of stem cells, e.g. at least 60% stem cells, more preferably one of at least 70% stem cells, 80% stem cells, 90% stem cells, 95% stem cells, 96% stem cells, 97% stem cells, 98% stem cells, 99% stem cells or 100% stem cells. Cells, e.g. cells collected from previous cell culture or from live animals or humans, may be enriched prior to initiating cell culture, e.g. by enriching for markers such as STRO-1 or STRO-1$^{bright}$. Marker enrichment may be performed by cell sorting, e.g. FACS.

In another aspect of the present invention an in vitro method of increasing the number of colony forming unit (CFUs) in a culture of stem cells is provided, the method comprising culturing stem cells in contact with heparan sulphate. The heparan sulphate is preferably HS-2. The method may involve increasing the % or proportion of CFUs contained in the culture.

The CFUs preferably express one or more of CD49a, CD73, CD105, CD90, STRO-1 and optionally do not express CD45.

In another aspect of the present invention there is provided a method for increasing the proportion of STRO-1$^{+bright}$ cells in an in vitro culture of mesenchymal stem cells, the method comprising culturing mesenchymal stem cells in contact with heparan sulphate. The heparan sulphate is preferably HS-2.

In another aspect of the present invention there is provided an in vitro method of preventing or reducing the loss of multipotent status of multipotent stem cells during stem cell expansion in in vitro culture, the method comprising culturing the stem cells in contact with heparan sulphate. The heparan sulphate is preferably HS-2.

The method may comprise maintaining the stem cells in culture for at least 10 population doublings, more preferably at least one of 15, 20, 25, 30, 35 or 40 population doublings. The method may comprise maintaining the stem cells in culture for no more than 50 population doublings.

In another aspect of the present invention there is provided an in vitro method of preventing or reducing shortening of telomere length in cultured stem cells comprising contacting stem cells in culture with heparan sulphate. The heparan sulphate is preferably HS-2. The method preferably does not involve the addition of telomere extension agents, for example addition or overexpression of hTERT.

In another aspect of the present invention there is provided an in vitro method of expanding a culture of stem cells from an initial number of stem cells to an expanded number of stem cells, wherein the expanded number is at least 100 times, preferably at least 1000 times, the initial number and wherein the time to expand the culture between the initial number and the expanded number is less than 30 days, more preferably less than one of 28, 26, 24, 22, 20, 18, 16, 15, 14, 13, 12, 11, 10, 9, 8, 7, 6 or 5 days.

The use of HS, preferably HS-2, in a method of culturing cells, preferably stem cells, in vitro is also provided. Culture media comprising HS-2 is also provided. The culture media may be of any kind but is preferably liquid or gel and may contain other nutrients and growth factors (e.g. FGF-2). The concentration of heparan sulfate in the culture media may range between about 1.0 ng/ml culture media to about 1000 ng/ml culture media. Preferably, the concentration of heparan sulphate in the culture media is between about 5 ng/ml culture media and 200 ng/ml culture media, more preferably between about 20 ng/ml culture media and 170 ng/ml culture media.

In another aspect of the present invention a method is provided comprising a method of promoting or facilitating proliferation and maintenance of stem cells in ex vivo (in vitro) culture, said method comprising the administration of a glycosaminoglycan or proteoglycan to said stem cells. The glycosaminoglycan may comprise heparan sulphate and may be HS-2. The glycosaminoglycan may be administered in solution or may be adsorbed to a matrix or scaffold component, e.g. a sponge, that is placed in contact with, or in close proximity to, the cells.

The concentration of the heparan sulfate may range between about 6.4 ng/ml culture media and about 20 µg/ml culture media. The heparan sulfate concentration may be about 160 ng/ml culture media.

Stem cells obtained by culture in HS are preferably of the same type (homogeneous cell culture) and are stem cells obtained by expansion of an initial culture of multipotent stem cells contacted with heparan sulphate, preferably HS-2.

Expansion of stem cells refers to the increase in population of stem cells in a culture, achieved through cell division. Expansion may be measured by a doubling in the population of stem cells in the culture and the rate of population doubling may be used as a measured of the rate of stem cell expansion. In methods of the present invention the rate of population doubling is preferably in the range about 0.5 PD/per day to about 1.2 PD/day, more preferably about 0.6 to about 0.9 PD/day, still more preferably about 0.6 to 0.8 PD/day. Between days 1 and 10 following addition of HS to the culture media the rate of population doubling is preferably between about 0.6 and about 0.8 PD/day.

Methods according to the present invention may comprise culturing stem cell(s) in culture media containing HS-2 at physiological temperatures and for a period of time sufficient to allow at least 5 population doublings, more preferably at least 10 population doublings. The culture period may be between 5 and 50 days.

As used herein, the expression "proliferation" or "proliferating" is used in its regular meaning and relates to the expansion of cells or tissue, including cell growth and cell division.

The term "maintenance" as used herein in relation to the culture of stem cells, refers to the preservation of the "stemness", i.e. the multipotentiality, and the viability of said stem cells in culture.

The methods of cell culture may comprise culture of cells in the linear (logarithmic) growth phase only, in post-confluent growth only, or may comprise growth extending over both linear and post-confluent phases. Preferably the methods of cell culture may comprise culture of cells in the linear (logarithmic) growth phase only.

The stem cells cultured and described herein may be stem cells of any kind. They may be totipotent or multipotent (pluripotent). They may be embryonic or adult stem cells from any tissue and may be hematopoietic stem cells, neural stem cells or mesenchymal stem cells. Preferably they are adult stem cells. More preferably they are adult mesenchymal stem cells, e.g. capable of differentiation into connective tissue and/or bone cells such as chondrocytes, osteoblasts, myocytes and adipocytes. The stem cells may be obtained from any animal or human, e.g. non-human animals, e.g. rabbit, guinea pig, rat, mouse or other rodent (including cells from any animal in the order Rodentia), cat, dog, pig, sheep, goat, cattle, horse, non-human primate or other non-human vertebrate organism; and/or non-human mammalian animals; and/or human. Optionally they are non-human.

In this specification, by stem cell is meant any cell type that has the ability to divide (i.e. self-renew) and remain totipotent or multipotent (pluripotent) and give rise to specialized cells if so desired.

Stem cells cultured in the present invention may be obtained or derived from existing cultures or directly from any adult, embryonic or fetal tissue, including blood, bone marrow, skin, epithelia or umbilical cord (a tissue that is normally discarded).

The multipotency of stem cells may be determined by use of suitable assays. Such assays may comprise detecting one or more markers of pluripotency, e.g. alkaline phosphatase activity, detection of RUNX2, osterix, collagen I, II, IV, VII, X, osteopontin, Osteocalcin, BSPII, SOX9, Aggrecan, ALBP, CCAAT/enhancer binding protein-α (C/EBPα), adipocyte lipid binding protein (ALBP), alkaline phosphatise (ALP), bone sialoprotein 2, (BSPII), Collagen2a1 (CoII2a) and SOX9.

Stem cells cultured in HS according to the present invention represent an enriched population of stem cells that maintain the multipotent status of the stem cells in the initiating culture. This is achieved without exogenous addition of factors intended to increase telomere length, such as overexpression of hTERT. Preferably the stem cells do not overexpress telomerase.

In this specification a culture of stem cells, or composition comprising stem cells, has preferably not been enriched by cell sorting, e.g. FACS sorting. A collection of cells enriched by cell sorting techniques, e.g. enriching for STRO-1 cells, is not considered to represent a "culture" of cells.

In yet a further aspect of the present invention, a pharmaceutical composition comprising stem cells generated by any of the methods of the present invention, or fragments or products thereof, is provided. The pharmaceutical composition useful in a method of medical treatment. Suitable pharmaceutical compositions may further comprise a pharmaceutically acceptable carrier, adjuvant or diluent. The pharmaceutical composition may comprises a scaffold or matrix material having cells implanted or adsorbed to the material. Such a composition may provide the basis of an implantable device or prosthesis, which may be surgically implanted into a patient in need of treatment.

In another aspect of the present invention, stem cells generated by any of the methods of the present invention may be used in a method of medical treatment, preferably, a method of medical treatment is provided comprising administering to an individual in need of treatment a therapeutically effective amount of a medicament or pharmaceutical composition containing stem cells.

Stem cells obtained through culture methods and techniques according to this invention may be used to differentiate into another cell type for use in a method of medical treatment. Thus, the differentiated cell type may be derived from, and may be considered as a product of, a stem cell obtained by the culture methods and techniques described which has subsequently been permitted to differentiate. Pharmaceutical compositions may be provided comprising such differentiated cells, optionally together with a pharmaceutically acceptable carrier, adjuvant or diluent. Such pharmaceutical compositions may be useful in a method of medical treatment.

Methods according to the present invention may be performed in vitro. The term "in vitro" is intended to encompass experiments with cells in culture whereas the term "in vivo" is intended to encompass experiments with intact multi-cellular organisms.

The patient or individual to be treated may be any animal or human. The patient is preferably a non-human mammal, more preferably a human patient. The patient may be male or female.

Unless defined otherwise, all technical and scientific terms used herein have a meaning as commonly understood by those of ordinary skill in the art to which the invention belongs. Although any method and material similar or equivalent to those described herein can be used in the practice or testing of the present invention, preferred methods and materials are described. For the purpose of the present invention, the following terms are defined below.

The listing or discussion of a prior-published document in this specification should not necessarily be taken as an acknowledgement that the document is part of the state of the art or is common general knowledge. All documents listed are hereby incorporated herein by reference.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which:

FIG. 15. Proportion of the linkages in HS-2 susceptible to low pH $HNO_2$, heparitinase and heparinase. Radiolabelled heparan sulfate was treated with low pH $HNO_2$, heparinase, or heparitinase and fractioned on a Bio-Gel P-10 column. The percentage of the total treatment-sensitive linkages was determined in two separate experiments by $\Sigma A_n/n$ where $A_n$ is the percentage of total radioactivity in that peak, and n is the number of disaccharide repeat units in the oligosaccharides as determined by the elution position (Turnbull and Gallagher, 1990; Kato et al. 1994).

FIG. 16. Nitrous acid-derived disaccharide composition of heparan sulfate from E10 neuroepithelia. Radiolabelled HS was depolymerized by deaminitive cleavage with low pH $HNO_2$. Disaccharides were isolated after $HNO_2$ treatment of the GAGs and the samples then run on a 1×120 cm Bio-Gel P-2 column. The resulting disaccharides were fractionated by SAX-HPLC. Areas under the peaks were integrated to give the disaccharide composition and subsequently, the percentage composition in each sample.

FIG. 17. Tetrasaccharides from $HNO_2$ treated HS-2 separated by SAX-HPLC. Tetrasaccharides derived from $HNO_2$ treated heparan sulfates were originally separated on a Bio-Gel P-2 column and were then further resolved on SAX-HPLC. The percentage of each was determined by calculating the radioactivity in each peak and comparing it to the total radioactivity in all peaks combined. Tetrasaccharide peak numbers in the left column correspond to the peaks from SAX-HPLC. The degree of sulfation was determined by comparison of these tritiated samples with peaks generated by dual $^{35}S/^3H$ radiolabelled samples (from Dr. Gordon Jayson, University of Manchester) run on the same column under identical conditions.

FIG. 18. Disaccharide composition of heparan sulfate from E10 neuroepithelium following heparin lyase treatment. Heparan sulfate was completely depolymerized with a mixture of heparan lyases. The resulting unsaturated disaccharides were isolated on a P-2 column and fractionated by strong anion exchange column chromatography. The area under each resultant curve was integrated to calculate the percentage of each disaccharide in each sample. Numbers represent the average of two runs (for the primary GAG samples) and three runs (for the 2.3D derived samples). Over 97% disaccharides were recovered from each sample.

FIG. 19. Sulfation characteristics of disaccharides from the HS pools shown in FIG. 18.

FIG. 24. The presence of FGF2 but not HS2 decreases adipogenic differentiation of hMSCs. At confluence hMSCs were changed to maintenance (control; ▲) or adipogenic media with or without (Differentiation control; ●) supplementation with 160 ng/ml HS2 (▼) or 10 ng/ml FGF2 (□). Cells were cultured for 32 days with a media change twice a week. A) Phase contrast photomicrograph (×200 magnification) of cells in the four differentiation conditions. Cells in maintenance media with or without supplements failed to accumulate lipid (data not shown). B) Adiponectin ELISA at every media change. Samples were collected, stored at −80° C. and analyzed in triplicate using an Adiponectin ELISA kit (Otsuka pharmaceutical) following the instructions from the manufacturer. HS had no adverse effect on adiponectin levels, compared to FGF-2, which greatly inhibited its expression across all time points.

FIG. 25. Presence of FGF2 but not HS2 decreases osteogenic differentiation of hMSCs. At confluence, media was changed to maintenance or osteogenic with or without (CTRL) supplementation with 160 ng/ml HS2 or 10 ng/ml FGF2. Cells were cultured for 21 days with a media change twice a week. Cells cultured in osteogenic media supplemented with FGF2 lifted from the plate after 16 days. A) Phase contrast photomicrograph (x200 magnification) of cells in the four differentiation conditions after 14 and 21 days. B) hMSC mineralization after 14 and 21 days as determined by alizarin red staining. Cells in maintenance media failed to mineralize (data not shown).

FIG. 26. hMSCs expanded for 21 days in HS-2 maintain their immunomodulatory capabilities. hMSCs expanded for 21 days in control or HS-2 containing media (FIG. 3a) were seeded at 10.000 cells/well in 96 well plates. The day after, a mixture of stimulatory and reactionary PBMCs from two different donors were added to the wells at different hMSC: PBMC ratios and the cells incubated for 6 days before the expression of CD3+ Ki67+ cells was assessed by FACS*. Stimulatory PBMCs were γ-irradiated (2,000 rads) to prevent any proliferation in response to the reactionary PBMCs, while reactionary PBMCs were left untreated. The positive control represents the maximum number of CD3+ Ki67+ cells obtained in the absence of hMSCs. All readings were taken in duplicate for each experiment and the graph shows the mean with the standard deviation of two separate experiments.

FIG. 27. Table 1—Taqman primer/probes used for quantitative PCR. ACC number=accession number in the Genbank database.

FIGS. 30 and 31. Table 2—List of genes identified by angle selection. Genes are sorted based on angles subtended by their loadings with respect to the origin and Euclidean distances greater than the 90-th percentile on the projection space defined by the 2 maximally-variant axes. Provided are Unigene Ids, Genbank RefSeq numbers, gene symbols and descriptions.

DETAILED DESCRIPTION OF THE INVENTION

Figure 1:
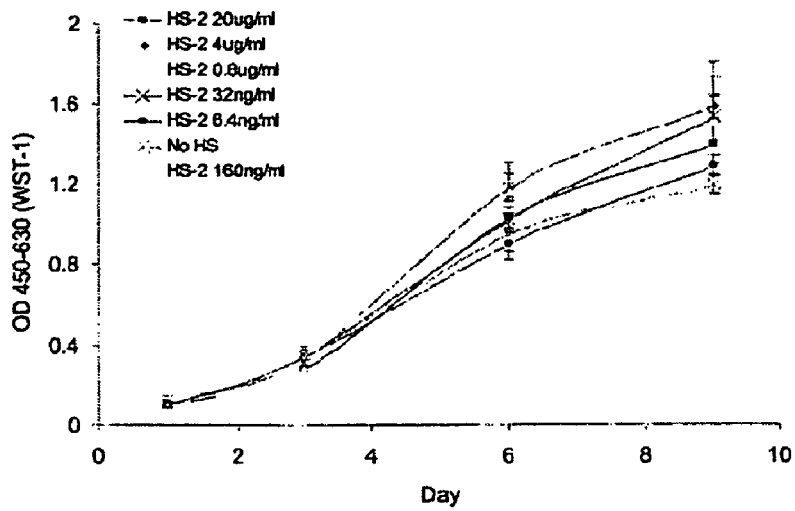
FIG. 1 shows the effect of different heparan sulphate 2 concentrations on human mesenchymal stem cell proliferation. Human mesenchymal stem cells were plated at 3300 cells/cm$^2$ in 96 well plates (NUNC) and cultured for 9 days in the presence of different concentrations of heparan sulphate 2. The metabolic activity was determined after 1, 3, 6 and 9 days of culture by WST-I assay (Roche).

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

Here we report on an embryonic HS preparation that is able to specifically induce the proliferation of a naïve hMSC subpopulation contained within a heterogeneous pool of adherent bone marrow cells. Furthermore, prolonged ex vivo expansion in HS yields therapeutic numbers of cells with increased proliferative and differentiative potential in much shorter periods of time.

We show that the recovery of CFU-Fs from primary bone marrow can be increased by using an embryonic heparan sulfate (HS-2) as a culture supplement. Importantly, HS-2 appears to specifically increase the proliferation of cells bearing the multipotency marker STRO-1 that has previously been reported to be highly expressed in CFU-Fs from the bone marrow[9,28], that correlates with our observations on the recovered CFU-Fs from the BMMNCs used here (FIG. 10d). For the expansion of the recovered CFU-Fs we show that the presence of HS-2 significantly increases the proliferation of the hMSCs. This has a significant impact on the culture time needed to obtain therapeutic numbers, as the presence of HS-2 can reduce this time by at least 35%. This estimate is entirely based on the rate of hMSC expansion (FIG. 11a); if the cells were recovered from the donor BMMNCs in the presence of HS-2, this reduction is even more significant (FIG. 10a). Comparing cultures at similar PDs shows that not only do the HS-2 expanded cultures contain significantly more multipotent hMSCs, but these cells also have longer average telomere lengths compared to control cultures. This implies that not only are the HS-2 expanded cultures more multipotent but they are also likely to have a longer life span in vivo, thus improving their therapeutic utility. Furthermore, despite achieving large-scale expansion of multipotent hMSCs using HS-2 supplementation, these cells retained their immunomodulatory capabilities[7] (FIG. 26). This demonstrates that one of the key characteristics of hMSCs, the ability to suppress the host immune response, is maintained after expansion in HS-2, and further highlights the therapeutic potential of this platform technology. Importantly, we also tested for karyotype stability after long-term culturing in HS-2; the results showed no karyotypic abnormalities in the hMSCs (data not shown).

We are also introducing here a different approach to assess stemness in expanded hMSCs. By applying a principal component analysis to gene array data, it is possible to exploit a statistical methodology that has previously been shown to be sensitive enough to discriminate between tumour subtypes, to create gene expression signatures. Until now, this method has never been used for the analysis of stem cells and our results clearly show that hMSCs expanded in HS-2 have a unique signature that is distinct from control cultures. Moreover, long-term expansion in HS-2 (45 days) creates a stem cell signature that resembles control cells from much earlier passages and suggests, in conjunction with the clonal assay, that HS-2 maintains the stemness of culture-expanded hMSCs. This maintenance of the stemness may result from an early amplification of a naïve subpopulation in the hMSC cultures.

The results described demonstrate HS-2 to specifically increase the proliferation of cells bearing the multipotency marker STRO-1 that has previously been reported to be highly expressed in CFU-Fs from the bone marrow[9,28], that correlates with our observations on the recovered CFU-Fs from the BMMNCs used here (FIG. 10d). For the expansion of the recovered CFU-Fs we show that the presence of HS-2 significantly increases the proliferation of the hMSCs. This has a significant impact on the culture time needed to obtain therapeutic numbers, as the presence of HS-2 can reduce this time by at least 35%. This estimate is based on the rate of hMSC expansion (FIG. 11a); if the cells were recovered from the donor BMMNCs in the presence of HS-2, this reduction is even more significant (FIG. 10a).

Comparing cultures at similar PDs shows that not only do the HS-2 expanded cultures contain significantly more multipotent hMSCs, but these cells also have longer average telomere lengths compared to control cultures. This implies that not only are the HS-2 expanded cultures more multipotent but they are also likely to have a longer life span in vivo, thus improving their therapeutic utility. Furthermore, despite achieving large-scale expansion of multipotent hMSCs using HS-2 supplementation, these cells retained their immunomodulatory capabilities[7] (FIG. 26). This demonstrates that one of the key characteristics of hMSCs, the ability to suppress the host immune response, is maintained after expansion in HS-2, and further highlights the therapeutic potential of this platform technology. Importantly, we also tested for karyotype stability after long-term culturing in HS-2; the results showed no karyotypic abnormalities in the hMSCs.

Highly charged HS molecules can be extracted and purified through a series of well-established enzymatic, chemical and chromatographic steps that preclude infectious agents such as bacteria, viruses and prions. In contrast to protein growth factors, HS is resilient to a range of bioprocessing procedures, being thermally stable and chemically resistant, making them particularly suited as culture reagents and for biotechnological applications.

This study supports the use of HS as a powerful conveyor of biological information in artificial environments, and further suggests a direction for its use in regenerative medicine. These highly charged HS molecules can be extracted and purified through a series of well-established enzymatic, chemical and chromatographic steps that preclude infectious agents such as bacteria, viruses and prions. In contrast to protein growth factors, HS is resilient to a range of bioprocessing procedures, being thermally stable and chemically resistant, making them particularly suited as culture reagents and for biotechnological applications.

Proteoglycans generally represent a special class of glycoproteins that are heavily glycosylated. They consist of a core protein with one or more covalently attached glycosaminoglycan (GAG) chain(s). These glycosaminoglycan chains are long, linear carbohydrate polymers that are negatively charged under physiological conditions, due to the occurrence of sulfate and uronic acid groups. Proteoglycans are a major component of the animal extracellular matrix. Therein, proteoglycans form large complexes, both to other proteoglycans and also to fibrous matrix proteins (such as collagen). They are also involved in binding cations (such as sodium, potassium and calcium) and water, and also regulate the movement of molecules through the matrix. Evidence also shows they can affect the activity and stability of proteins and signaling molecules within the matrix. Individual functions of proteoglycans can be attributed to either the protein core or the attached GAG chain.

Growth factors binding to proteoglycans of the extracellular matrix have been shown to regulate both differentiation and proliferation of human stem cells in vitro and in vivo. These growth factors signal through interaction with specific plasma membrane receptor kinases, an interaction that may involve proteoglycan binding. However, existing methods of using growth factors, such as FGF, have the drawback that while stimulating stem cell proliferation, the growth factor addition leads to a significant loss of multipotentiality of the stem cells. In contrast and surprisingly, the observed proliferation increase achieved according to the methods of the present invention is accompanied by the preservation of the multipotentiality of the stem cells.

Proteoglycans can be used in accordance to the present invention, even though they may in some embodiments not be as conveniently used as the corresponding glycosaminoglycans, because the saccharide chains have been found to be easier to handle, i.e. smaller and more stable, more soluble and less prone to interfering interactions, for example with the extracellular matrix. Therefore, the glycosaminoglycans have an increased bioactivity per microgram compared to the proteoglycans.

Thus, in preferred aspects of the invention the glycosaminoglycan or proteoglycan is preferably a glycosaminoglycan, and more preferably a heparan sulfate.

Heparan sulfate proteoglycans (HSPGs) represent a highly diverse subgroup of proteoglycans and are composed of heparan sulfate glycosaminoglycan side chains covalently attached to a protein backbone. The core protein can exist in three forms: a secreted form known as perlecan, a form anchored in the plasma membrane known as glypican, and a transmembrane form known as syndecan. They are uniquitous constituents of mammalian cell surfaces and most extracellular matrices.

"Heparan sulphate" ("Heparan sulfate" or "HS") is initially synthesised in the Golgi apparatus as polysaccharides consisting of tandem repeats of D-glucuronic acid (GlcA) and N-acetyl-D-glucosamine (GlcNAc). The nascent polysaccharides may be subsequently modified in a series of steps: N-deacetylation/N-sulfation of GlcNAc, C5 epimerisation of GlcA to iduronic acid (IdoA), O-sulphation at C2 of IdoA and GlcA, O-sulphation at C6 of N-sulphoglucosamine (GlcNS) and occasional O-sulphation at C3 of GlcNS. N-deacetylation/N-sulphation, 2-O-, 6-O- and 3-O-sulphation of HS are mediated by the specific action of HS N-deacetylase/N-sulfotransferase (HSNDST), HS 2-O-sulfotransferase (HS2ST), HS 6-O-sulfotransferase (HS6ST) and HS 3-O-sulfotransferase, respectively. At each of the modification steps, only a fraction of the potential substrates are modified, resulting in considerable sequence diversity. This structural complexity of HS has made it difficult to determine its sequence and to understand the relationship between HS structure and function.

Heparan sulfate side chains consist of alternately arranged D-glucuronic acid or L-iduronic acid and D-glucosamine, linked via (1->4) glycosidic bonds. The glucosamine is often N-acetylated or N-sulfated and both the uronic acid and the glucosamine may be additionally O-sulfated. The specificity of a particular HSPG for a particular binding partner is created by the specific pattern of carboxyl, acetyl and sulfate groups attached to the glucosamine and the uronic acid. In contrast to heparin, heparan sulfate contains less N- and O-sulfate groups and more N-acetyl groups. The heparan sulfate side chains are linked to a serine residue of the core protein through a tetrasaccharide linkage (-glucuronosyl-β-(1→3)-galactosyl-β-(1→3)-galactosyl-β-(1→4)-xylosyl-β-1-O-(Serine)) region.

Both heparan sulfate chains and core protein may undergo a series of modifications that may ultimately influence their biological activity. Complexity of HS has been considered to surpass that of nucleic acids (Lindahl et al, 1998, J. Biol. Chem. 273, 24979; Sugahara and Kitagawa, 2000, Curr. Opin. Struct. Biol. 10, 518). Variation in HS species arises from the synthesis of non-random, highly sulfated sequences of sugar residues which are separated by unsulfated regions of disaccharides containing N-acetylated glucosamine. The initial conversion of N-acetylglucosamine to N-sulfoglucosamine creates a focus for other modifications, including epimerization of glucuronic acid to iduronic acid and a complex pattern of O-sulfations on glucosamine or iduronic acids. In addition, within the non-modified, low sulfated, N-acetylated sequences, the hexuronate residues remain as glucuronate, whereas in the highly sulfated N-sulfated regions, the C-5 epimer iduronate predominates. This limits the number of potential disaccharide variants possible in any given chain but not the abundance of each. Most modifications occur in the N-sulfated domains, or directly adjacent to them, so that in the mature chain there are regions of high sulfation separated by domains of low sulfation (Brickman et al. (1998), J. Biol. Chem. 273(8), 4350-4359, which is herein incorporated by reference in its entirety).

It is hypothesized that the highly variable heparan sulfate chains play key roles in the modulation of the action of a large number of extracellular ligands, including regulation and presentation of growth and adhesion factors to the cell, via a complicated combination of autocrine, juxtacrine and paracrine feedback loops, so controlling intracellular signaling and thereby the differentiation of stem cells. For example, even though heparan sulfate glycosaminoglycans may be genetically described (Alberts et al. (1989) Garland Publishing, Inc, New York & London, pp. 804 and 805), heparan sulfate glycosaminoglycan species isolated from a single source may differ in biological activity. As shown in Brickman et al, 1998, Glycobiology 8, 463, two separate pools of heparan sulfate glycosaminoglycans obtained from neuroepithelial cells could specifically activate either FGF-1 or FGF-2, depending on mitogenic status. Similarly, the capability of a heparan sulfate (HS) to interact with either FGF-1 or FGF-2 is described in WO 96/23003. According to this patent application, a respective HS capable of interacting with FGF-1 is obtainable from murine cells at embryonic day from about 11 to about 13, whereas a HS capable of interacting with FGF-2 is obtainable at embryonic day from about 8 to about 10.

As stated above HS structure is highly complex and variable between HS. Indeed, the variation in HS structure is considered to play an important part in contributing toward the different activity of each HS in promoting cell growth and directing cell differentiation. The structural complexity is considered to surpass that of nucleic acids and although HS structure may be characterised as a sequence of repeating disaccharide units having specific and unique sulfation patterns at the present time no standard sequencing technique equivalent to those available for nucleic acid sequencing is available for determining HS sequence structure. In the absence of simple methods for determining a definitive HS sequence structure HS molecules are positively identified and structurally characterised by skilled workers in the field by a number of analytical techniques. These include one or a combination of disaccharide analysis, tetrasaccharide analysis, HPLC and molecular weight determination. These analytical techniques are well known to and used by those of skill in the art.

Two techniques for production of di- and tetra-saccharides from HS include nitrous acid digestion and lyase digestion. A description of one way of performing these digestion techniques is provided below, purely by way of example, such description not limiting the scope of the present invention.

Nitrous Acid Digestion

Nitrous acid based depolymerisation of heparan sulphate leads to the eventual degradation of the carbohydrate chain into its individual disaccharide components when taken to completion.

For example, nitrous acid may be prepared by chilling 250 µl of 0.5 M $H_2SO_4$, and 0.5 M $Ba(NO_2)_2$ separately on ice for 15 min. After cooling, the $Ba(NO_2)_2$ is combined with the $H_2SO_4$ and vortexed before being centrifuged to remove the barium sulphate precipitate. 125 µl of $HNO_2$ was added to GAG samples resuspended in 20 µl of $H_2O$, and vortexed before being incubated for 15 min at 25° C. with occasional mixing. After incubation, 1 M $Na_2CO_3$ was added to the sample to bring it to pH 6. Next, 100 µl of 0.25 M $NaBH_4$ in 0.1 M NaOH is added to the sample and the mixture heated to 50° C. for 20 min. The mixture is then cooled to 25° C. and acidified glacial acetic acid added to bring the sample to pH 3. The mixture is then neutralised with 10 M NaOH and the volume decreased by freeze drying. Final samples are run on a Bio-Gel P-2 column to separate di- and tetrasaccharides to verify the degree of degradation.

Lyase Digestion

Heparinase III cleaves sugar chains at glucuronidic linkages. The series of Heparinase enzymes (I, II and III) each display relatively specific activity by depolymerising certain heparan sulphate sequences at particular sulfation recognition sites. Heparinase I cleaves HS chains with NS regions along the HS chain. This leads to disruption of the sulphated domains. Heparinase III depolymerises HS with the NA domains, resulting in the separation of the carbohydrate chain into individual sulphated domains. Heparinase II primarily cleaves in the NA/NS "shoulder" domains of HS chains, where varying sulfation patterns are found. (Note: The repeating disaccharide backbone of the heparan polymer is a uronic acid connected to the amino sugar glucosamine. "NS" means the amino sugar is carrying a sulfate on the amino group enabling sulfation of other groups at C2, C6 and C3. "NA" indicates that the amino group is not sulphated and remains acetylated.)

For example, for depolymerisation in the NA regions using Heparinase III both enzyme and lyophilised HS samples are prepared in a buffer containing 20 mM Tris-HCL, 0.1 mg/ml BSA and 4 mM $CaCl_2$ at pH 7.5. Purely by way of example, Heparinase III may be added at 5 mU per 1 µg of HS and incubated at 37° C. for 16 h before stopping the reaction by heating to 70° C. for 5 min.

Di- and tetrasaccharides may be eluted by column chromatography.

In one aspect of the invention the heparan sulfate is preferably heparan sulfate 2 (HS2). HS2 denominates the sugar chains of an HSPG, which have been found to have affinity for FGF-2. HS2 has a molecular weight of approximately 25 kDa and thus, assuming an average molecular mass of 400 Da per disaccharide, consists of about 60 disaccharides. The disaccharide composition of HS2 is set forth in Brickman et al. (Glycobiology Vo. 8 No. 5 pp. 463-471, 1998), which is herein incorporated by reference in its entirety.

By "heparan sulfate 2" or "HS2" is meant the heparan sulfate that is described by Brickman et al. (1998), J. Biol.

Chem. 273(8), 4350-4359) and that is capable of interacting with FGF-2. Accordingly, this heparan sulfate 2 is obtainable from heparan proteoglycans of murine cells at embryonic day 10 as described by Brickman (supra). The HS2 that is used in the experimental section of the present application is derived from embryonic mouse, it has been found to be very potent on mouse, human, rat, chicken, Xenopus and drosophila cells. In line with these results a universal mechanism amongst any higher organism (for example insects or vertebrates such as mammals, birds, reptiles or fish) is contemplated here. Thus, any heparan sulfate 2 and any respective heparan sulfate proteoglycan that is capable of interacting with FGF-2 and that is able to promote or facilitate proliferation and/or maintenance of stem cells ex vivo (in vitro) is encompassed in the present invention, including such heparan sulfate proteoglycan and heparan sulfate 2 that is yet to be isolated from a specific species. The isolation and determination of the functionality of the isolated heparan sulfate or heparan sulfate proteoglycan is well within the knowledge of the person of average skill in the art and can be carried out as described by Brickman et al. (1998), J. Biol. Chem. 273(8), 4350-4359, for example.

Figures 13, 14:
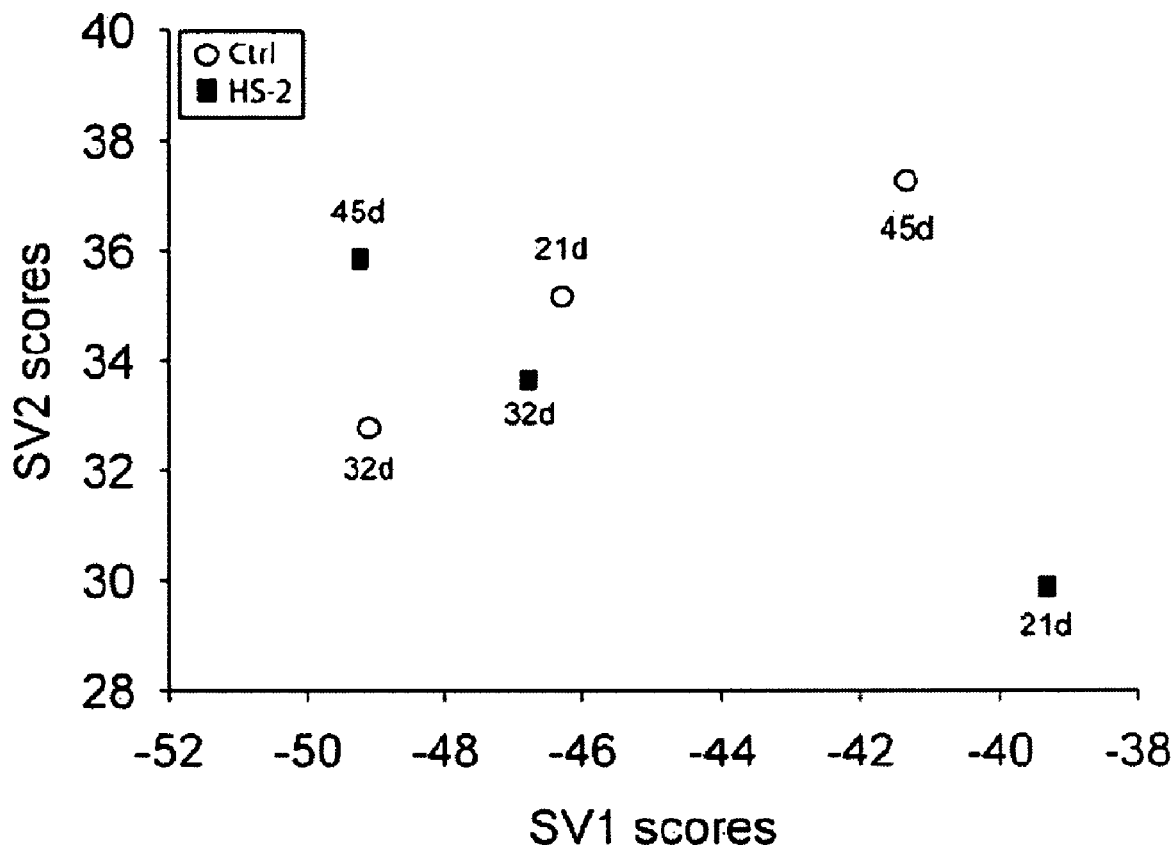
FIG. 13. HS-2 protects hMSC cultures against the temporal lose of stem cell gene expression. Singular value decomposition analysis of stem cell related gene expression measured by chemiluminescent GEArray (Stem Cell SuperArray #HS601.2, www.superarray.com). Data were log-transformed and corrected for cross-chip variations. (See description herein of singular value decomposition (SVD)).
FIG. 14. A summary of the estimated $M_r$ of extracellular-HS2 from E10 neuroepithelium. The source of HS was subjected to separation on a 1×120 cm Sepharose CL-6B column after a variety of treatments. The size of purified full length HS was determined both before and after mild alkali treatment to determine the presence of more than one chain per protein core. In addition, the approximate distance between heparinase-sensitive disaccharides was determined by isolating the non-resolved, large oligosaccharides from a Bio-Gel P-10 column and rerunning them on a Sepharose CL-6B column.

HS-2 can be obtained from embryonic day 10 (E10) mouse neuroepithelium. The molecular weight of HS-2 is shown in FIG. 14 following a variety of treatments including pronase treatment to remove any associated protein component, mild alkali and heparinase. HS-2 can be further characterised by analysis of the percentage of linkages sensitive to treatment with either low pH $HNO_2$, heparatinase or heparinase. The results are shown in FIG. 15. The disaccharide composition of HS-2 following nitrous acid digestion is shown in FIG. 16. The tetrasaccharide composition of HS-2 following nitrous acid digestion is shown in FIG. 17. The disaccharide composition of HS-2 following treatment with a mixture of heparin lyases is shown in FIG. 18. The sulfation characteristics of the disaccharides shown in FIG. 18 are shown in FIG. 19. Methodology for determining the percentage of linkages sensitive to susceptible treatment with either low pH $HNO_2$, heparatinase or heparinise; nitrous acid digestion and heparin lyase digestion are described elsewhere in this application.

In this specification reference to HS-2 includes HS obtained from embryonic day 10 (E10) mammalian neuroepithelium, preferably mouse. Reference to HS-2 may also include HS having substantially similar structure and/or function to HS-2 set forth in Brickman et al. in Glycobiology Vo. 8 No. 5 pp. 463-471, 1998. HS of substantial similarity to HS-2 of Brickman et al, may include HS having:

(i) a molecular weight no more than 10%, more preferably 5%, greater or less than the molecular weight shown in FIG. 14 for the corresponding treatment; and/or
(ii) a percentage of linkages susceptible to low pH nitrous acid, heparatinase or heparinase treatment that is no more than 10%, more preferably 5%, greater or less than the percentage shown in FIG. 15 for the corresponding treatment; and/or
(iii) a nitrous acid digestion disaccharide composition wherein each disaccharide corresponding to those shown in FIG. 16 is present and the percentage composition of each disaccharide is no more than 20%, more preferably 15%, 10%, 5%, 3%, 2% or 1%, greater or less than the percentage composition shown in FIG. 16; and/or
(iv) a nitrous acid digestion tetrasaccharide composition wherein each tetrasaccharide corresponding to those shown in FIG. 17 is present and the percentage composition of each tetrasaccharide is no more than 15%, more preferably 15%, 10%, 5%, 3%, 2% or 1%, greater or less than percentage composition shown in FIG. 17; and/or
(v) a heparin lyase disaccharide composition wherein each disaccharide corresponding to those shown in FIG. 18 is present and the percentage composition of each disaccharide is no more than 20%, more preferably 15%, 10% or 5%, greater or less than the percentage composition shown in FIG. 18.

Mesenchymal stem cells or human bone marrow stromal stem cells are defined as pluripotent (multipotent) progenitor cells with the ability to generate cartilage, bone, muscle, tendon, ligament and fat. These primitive progenitors exist postnatally and exhibit stem cell characteristics, namely low incidence and extensive self-renewal potential. These properties in combination with their developmental plasticity have generated tremendous interest in the potential use of adult mesenchymal stem cells to replace damaged tissues, such as damaged heart muscle. In essence mesenchymal stem cells could be cultured to expand their numbers then transplanted to the injured site or after seeding in/on scaffolds to generate appropriate tissue constructs.

Thus, an alternative approach for skeletal, muscular, tendon and ligament repair is the selection, expansion and modulation of the appropriate progenitor cells such as osteoprogenitor cells in the case of bone in combination with a conductive or inductive scaffolds to support and guide regeneration together with judicious selection of specific tissue growth factors.

Human bone marrow mesenchymal stem cells can be isolated and detected using selective markers, such as STRO-1, from a CD34+ fraction indicating their potential for marrow repopulation. These cell surface markers are only found on the cell surface of mesenchymal stem cells and are an indication of the cells pluripotency.

In the ex vivo (in vitro) culture of stem cells a major disadvantage raises from the fact that a change in the microenvironment from that normally found in the naive stem cell niche results in the spontaneous differentiation of stem cells in culture. The microenvironment of the stem cell niche is a complex pattern of signals from interactions with specific components of the extracellular matrix (ECM), neighboring cells and hormones.

The biochemical cues directing the fate of a cell in the niche are composed of growth factors and their co-factors. Certain species of glycosaminoglycans (GAGs) have been previously shown to have a mitogenic effect on breast cancer cells by signaling through FGF receptor 1 (FGFR1) (Nurcombe et al. (2000) J. Biol. Chem. 275(39), 30009-30018).

As FGFR1 is also expressed on human mesenchymal stem cells (hMSCs), it was found in the present invention that the addition of glycosaminoglycans together with growth factors (in form of FCS supplementation) to a culture of bone marrow derived adult human mesenchymal stem cells could optimize the culture conditions for growth and differentiation of these cells.

For the experiments carried out, a specific heparan sulfate glycosaminoglycan (HS) heparan sulfate 2 (HS2) as defined above was used. However, the heparan sulfate 2 used in the invention may be isolated from any suitable source, for example from precursor cells other than murine (e.g. human, pig, bovine, rat, chicken, drosophila, Xenopus, zebra fish, dog to name only a few illustrative examples) using, for example, the method of isolating as described in WO 96/23003 or by Brickman et al. (supra).

It has been demonstrated in the present invention that adding heparan sulfate 2 (HS2) to mesenchymal stem cells is able to increase proliferation of human mesenchymal stem cells.

HS2 was purified by standard chromatographic and enzymatic procedures from media collected from E9-10 mouse embryonic neuroepithelial cell cultures (Nurcombe et al. (1993) Science 260, 103-106, which is incorporated in its entirety by reference herein).

In the present invention, it has been demonstrated for the first time that the presence of heparan sulfate 2 increases the proliferation of hMSCs by several orders of magnitude compared to control cultures, simultaneously also increasing the total lifespan. This increase in proliferation was not associated with a relative loss of stem cells, as measured by colony forming units, expression of stem cell markers and multipotentiality assays.

Thus, heparan sulfate 2 may prove to be a valuable tool for the ex vivo propagation of stem cells, maintenance of "stemness" and specific cell differentiation and thus help unlock the potential use of stem cells for therapy and tissue repair.

EXAMPLE 1

To test the effect of specific heparan sulfate extracts on adult stem cell proliferation human mesenchymal stem cells (Poietics, Cambrex) were cultured in DMEM low glucose +10% fetal calf serum (FCS) (maintenance media) in the presence or absence of different concentrations of heparan sulfate 2. Cells were analyzed for metabolic activity by WST-1 assay (Roche). The results demonstrate that in one embodiment a HS2 concentration of about 160 ng/ml is the most mitogenic concentration and that higher doses are inhibitory (FIG. 1). Although 160 ng/ml appears to be the optimal concentration of HS2, HS2 was still effective to proliferate mesenchymal stem cells at concentrations ranging from 6.4 ng/ml to 20 µg/ml.

Figure 2:
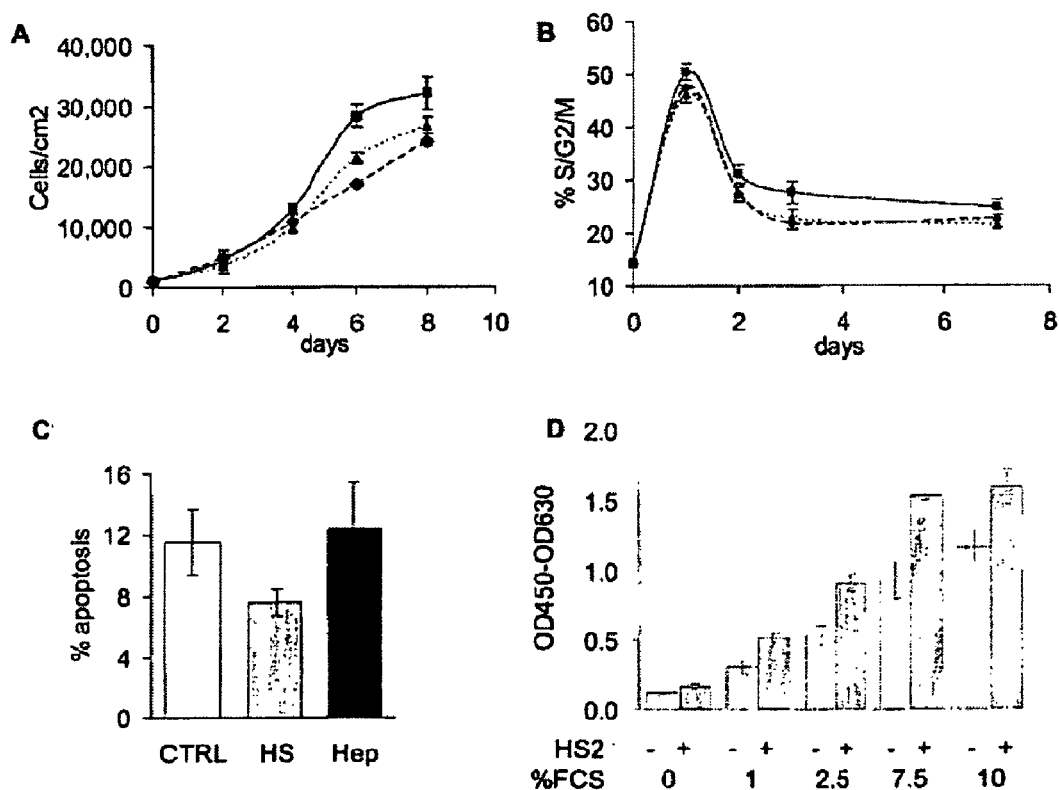
FIG. 2 illustrates the effect of heparan sulphate 2 on human mesenchymal stem cell proliferation in short term cultures. hMSC (Cambrex) were seeded in control media (DMEM, 1000 mg/l glucose, 10% fetal calf serum (Hyclone), penicillin/streptomycin, 2 mM L-Glutamine), serum starved for 48 hours in media containing 0.2% FCS and changed to control media (dotted line and open bars) or media containing 160 ng/ml HS2 (solid line and grey bars) or heparin (striped line and black bars) the day after (day 0). A. Heparan sulphate 2 increases the proliferation of human mesenchymal stem cells. Cell numbers were determined every second day using ViaCount software and staining with FLEX reagent (GUAVA technologies) on GUAVA PCA-96 flow cytometer following the instruction from the manufacturer. B. Heparan sulfate 2 increases the cell cycle numbers of human mesenchymal stem cells. hMSC were plated at 5000 cells/cm$^2$ and analyzed for DNA content after 1, 2, 3, 4 and 7 days. Cells were lifted with trypsin and counted as above, washed in PBS, 1 mM EDTA and fixed in 100% ice cold methanol. Cells were washed in PBA and stained with a solution of PI, RNaseA, Triton-X and analyzed on GUAVA PCA-96. C. Heparan sulfate decreases the percentage of cells undergoing apoptosis. hMSC were plated at 3300 cells/cm$^2$ and viability and apoptosis was determined after 9 days. Cells were stained using Annexin kit (GUAVA technologies) and analyzed on GUAVA PCA-96 flow cytometer. D. Effects of different FCS concentrations on proliferation of human mesenchymal stem cells in the presence or absence of heparan sulphate 2 (HS2). hMSCs were plated at 3300 cells/cm$^2$ in 96 well plates, cultured in media containing 0, 1, 2.5, 7.5 or 10% FCS and the metabolic activity was determined after nine days in culture using WST-1 kit (Roche). Every point or bar in the figures represents the average and standard deviation of at least three independent cultures each measured in triplicate.

In short term culture, the (optimal) dose of 160 ng/ml increased the number of cells by 65% at sub-confluency (FIG. 2A, day 6) and part of this increase was due to a decrease in apoptosis (FIG. 2C), as determined by flow cytometric assays. However, most of this increase is due to a higher number of cells entering the cell cycle at a given time as shown in FIG. 2B.

Figure 6:
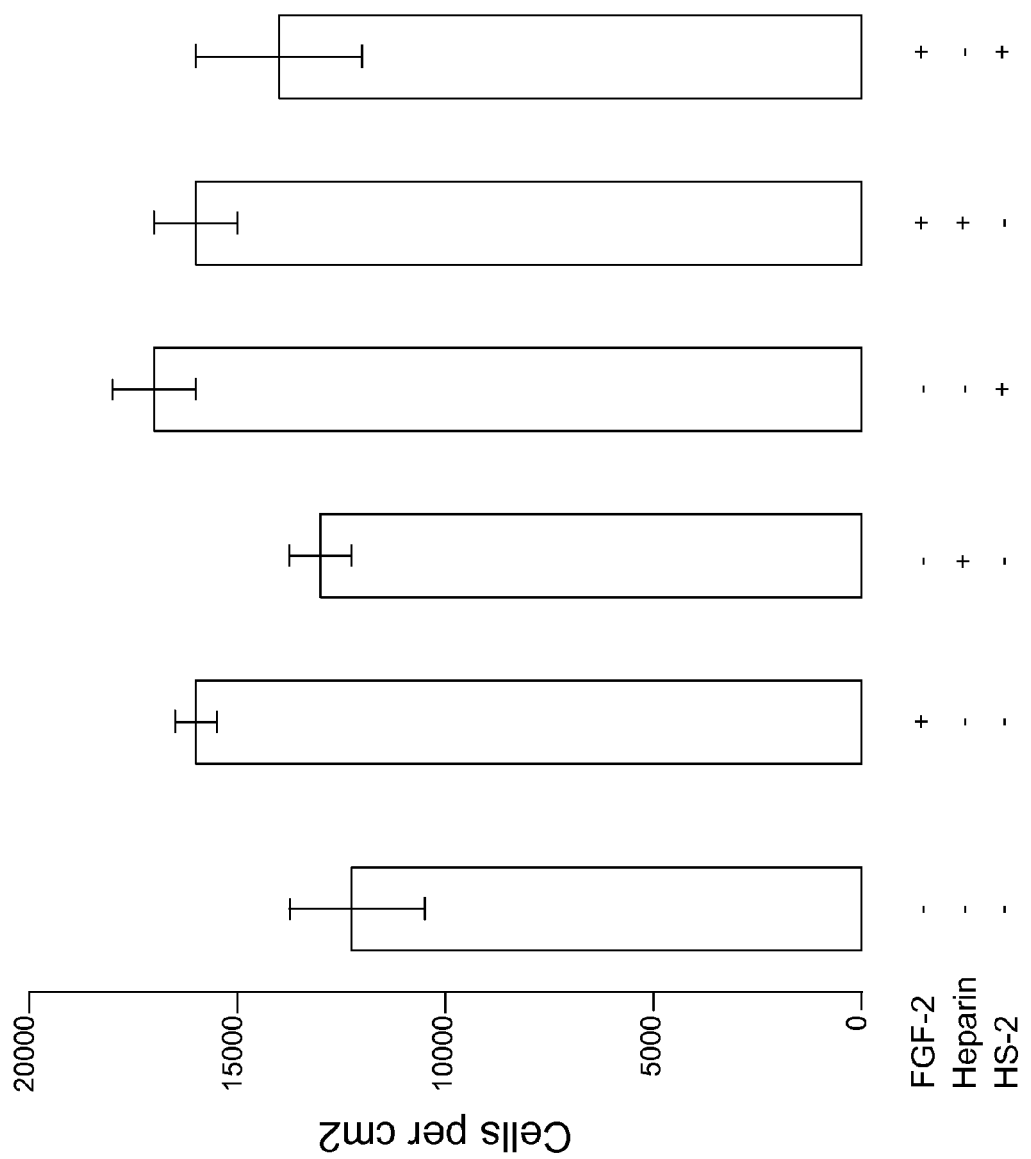
FIG. 6 illustrates the mitogenic effect of heparan sulphate 2 and FGF-2 on human mesenchymal stem cells. hMSCs were plated at 3300 cells/cm$^2$ in 24 well plates (NUNC) and cultured for 9 days in the presence or absence of 160 ng/ml heparan sulphate 2 (HS2), 160 ng/ml of heparin and 10 ng/ml of FGF-2 as well as combinations of FGF-2 with HS2 or heparin.
Figure 7:
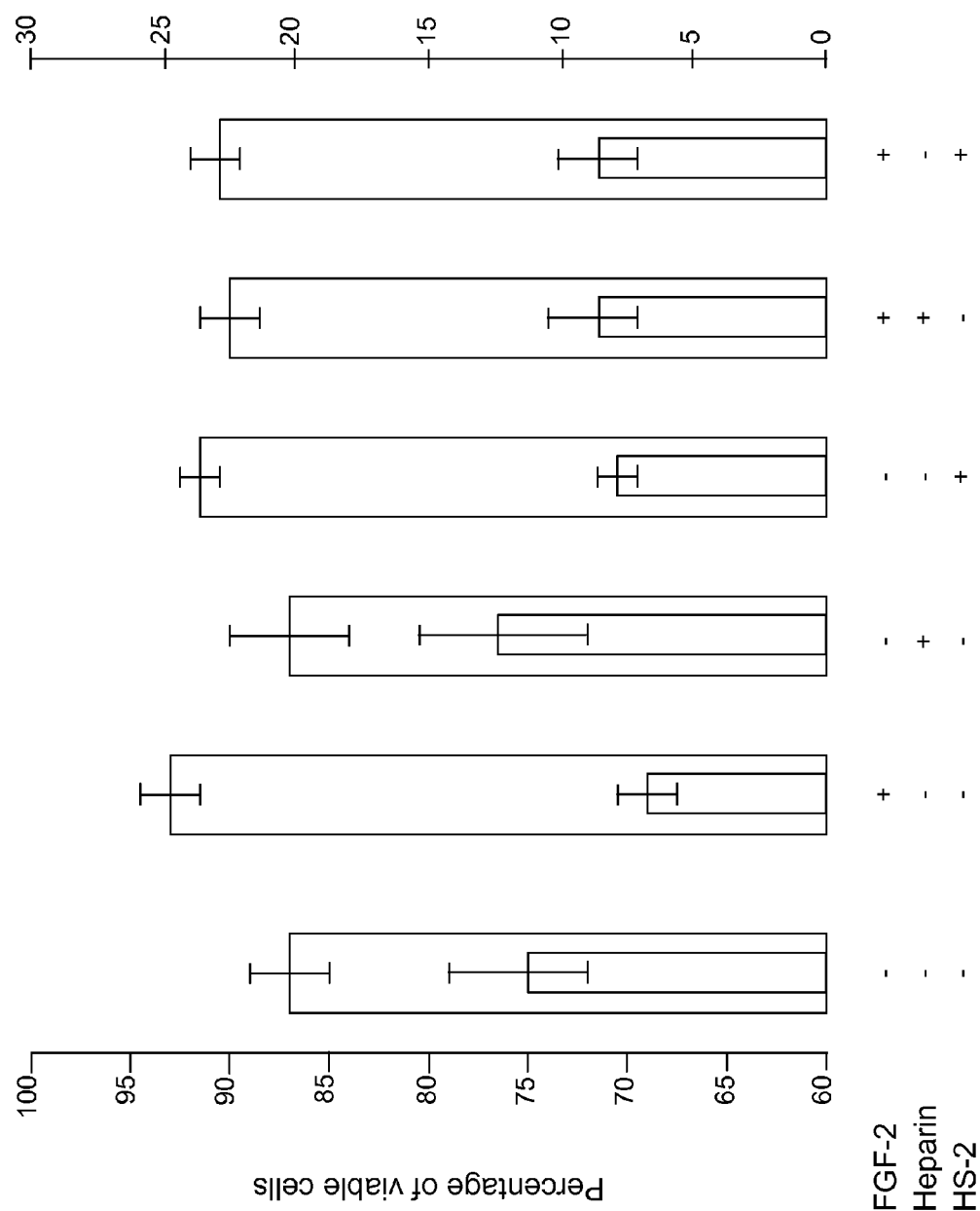
FIG. 7 illustrates the effect of heparan sulphate 2 and FGF-2 on human mesenchymal stem cell survival. Human mesenchymal stem cells were plated at 3300 cells/cm$^2$ in 24 well plates (NUNC) and cultured for 9 days in the presence or absence of 160 ng/ml heparan sulphate 2,160 ng/ml of heparin and 10 ng/ml of FGF-2 as well as combinations of FGF-2 with HS2 or heparin. The viability and apoptosis of the cells in culture were tested by Annexin V flow cytometry.

At the optimal concentration of HS2, the increase in proliferation of human mesenchymal stem cells is comparable to the effect observed in the presence of 10 ng/ml of FGF-2, a known mitogen (FIG. 6). In addition to its mitogenic properties, FGF 2 is also known to protect against apoptosis. Because Heparan sulfate 2 (HS2) displayed properties similar to FGF-2 it was investigated if protection against apoptosis contributed to the increase in cell number observed. It could be demonstrated that the increase in proliferation is associated with a decrease in apoptosis (FIG. 7).

Also investigated was the importance of FCS supplementation in mediating HS2 effect. As shown in FIG. 2D, HS2 has a mitogenic effect even at FCS concentration as low 1%. However, HS2 was not able to significantly increase the number of cells in serum starve condition over a short period of time.

Figure 3:
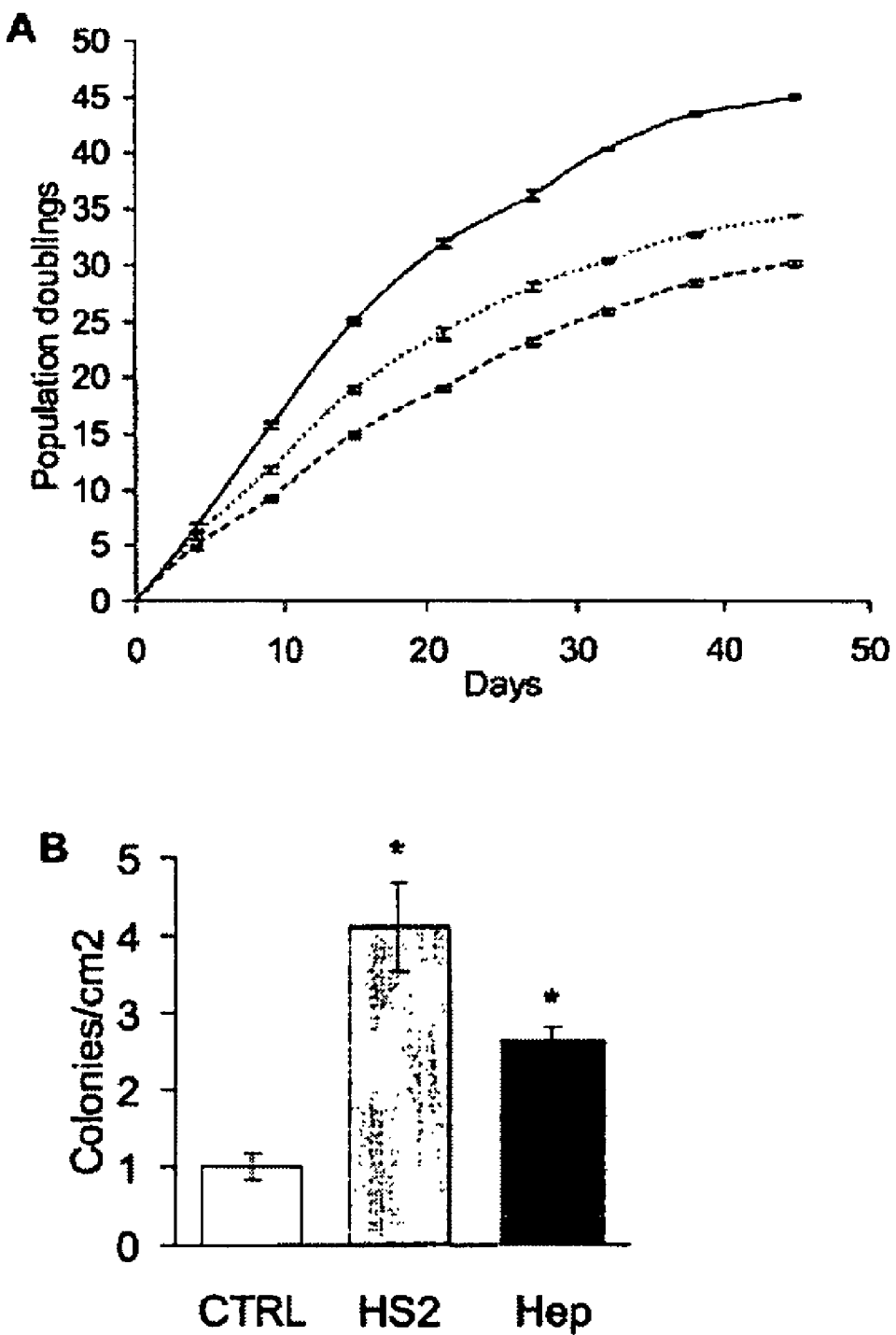
FIG. 3 illustrates that HS2 increases the life span and maintains the stemness of human mesenchymal stem cell cultures. Low passage hMSC were plated at 5000 cells/cm$^2$, changed to and maintained in control media (striped line and open bars) or media containing 160 ng/ml HS2 (solid line and grey bars) or heparin (dotted line and black bars) the day after (day 0). Cells were cultured until sub-confluence and at every passage cells were lifted with trypsin, counted and reseeded at 5000 cells/cm$^2$. A. Cumulative cell counts from every passage. hMSCs were plated at 5000 cells/cm$^2$ and cultured in DMEM+10% FCS without (ctrl) or with addition of 160 ng/ml HS2 or heparin. At every passage cells were counted by GUAVA viacount (two samples in triplicate), and reseeded at a density of 5000 cells/cm$^2$. B. Cells from the three cultures at population doubling 25 to 27 were seeded at a density of 30 cells/cm$^2$ in 24 well plates and cultured for 12 days in maintenance media. Cells were fixed in methanol, stained with Giemsa and colonies with more than 50 cells were counted. Each bar represents the average and standard deviation of the sum of colonies/cm$^2$. Every point or bar in the figures represents the average and standard deviation of at least three independent cultures each measured in triplicate.

The overall increase in proliferation of the hMSCs cultured in the presence of HS2 implicates that for a given period of time they undergo more population doubling (PD). Since PD is limited in these cells, it was expected that they reach replicative senescence earlier if kept in culture for a long term. Surprisingly, it was demonstrated that cells proliferation slowed down after a similar time in culture as the control but yielded 50% more population doubling after 45 days in culture (FIG. 3A). Since FGF-2 was shown to increase telomerase activity in neural precursor cells (Haik et al. (2000) Oncogene 19, 2957-2966), it was verified if any residual activity was present in the hMSCs. However, in accordance with previous results (Shi et al. (2002) Nature Biotechnol. 20, 587-591; Simonsen et al. (2002) Nature Biotechnol. 20, 592-596; Yudoh et al. (2001) J. Bone Miner. Res. 16, 1453-1464) no telomerase activity could be detected in these cells, suggesting that HS2 is targeting a population of cells harboring a greater doubling potential, likely the most naive cells in this population.

The hallmark of the most "stem-like" cells in the heterogeneous hMSC population is their ability to form colonies when seeded at low density thus providing a phenotype to confirm the effect of HS2. Therefore, a colony forming assay was set up and the results showed that hMSCs cultured with HS2 were able to form 5 times more colonies when compared to the control (FIG. 3B) and the difference is greater if the FCS concentration is reduced.

Figure 4:
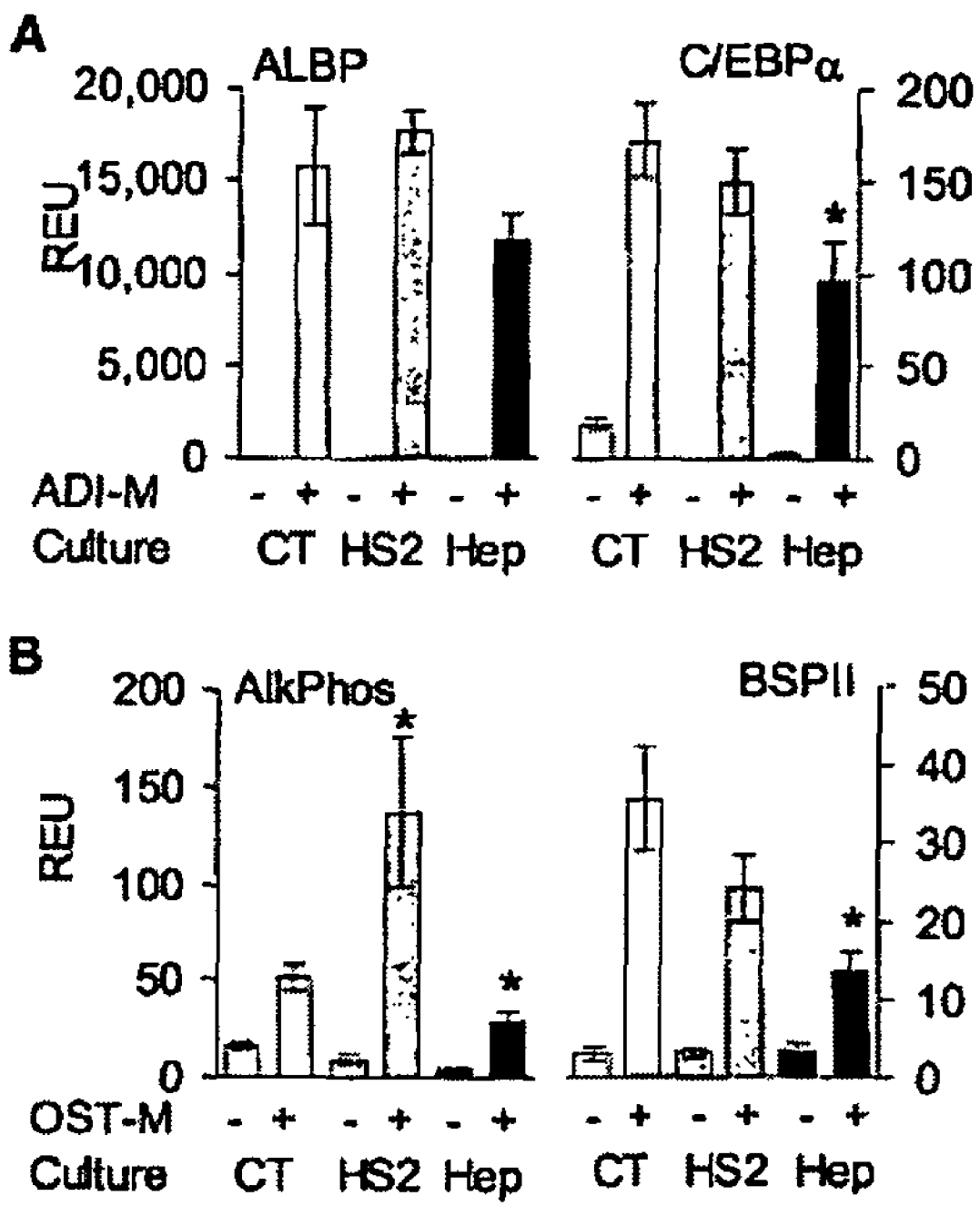
FIG. 4 illustrates the effects of heparan sulphate 2 on adipocyte and osteoblast differentiation. A. hMSCs from carry on cultures in media with or without 160 ng/ml heparan sulphate 2 (HS2) or heparin (Hep) were seeded at 18,000 cells/cm$^2$ in 12 well plates at passage +4. Cells were cultured to confluence, changed to adipogenic (DMEM with 10% FCS, 10 µg/ml insulin, 0.5 mM methylisobutylxanthine, 1 µM Dexamethasone) or control media and cultured for 23 days. RNA was isolated and purified using Machery Nagel Nucleospin2 kit, quantified and 250 µl used for reverse transcription using superscript. 80 ng cDNA were used as template for real time PCR with Taqman primer probes specific for adipogenic RNA markers adipocyte fatty acid binding protein (ALBP) and CCAAT/enhancer binding protein alpha (C/EBPα). The relative expression levels (REU) are normalized to the expression of 18S and multiplied by 10$^6$. B. hMSCs from carry on cultures in media with or without 160 ng/ml heparan sulphate 2 (HS2) or heparin (Hep) were seeded at 3,000 cells/cm$^2$ in 12 well plates at passage +4. Cells were cultured to confluence, changed to osteogenic (10 nM dexamethazone, 50 µM glycerophosphate and 100 µM L-ascorbate) or control media and cultured for 27 days. RNA was isolated and purified using Machery Nagel Nucleospin2 kit, quantified and 250 µl used for reverse transcription using superscript. 80 ng cDNA were used as template for real time PCR with Taqman primer probes specific for osteogenic RNA markers alkaline phosphatase and bone sialo protein II (BSPII). The relative expression levels (REU) are normalized to the expression of 18 S and multiplied by 106.

Osteogenesis and adipogenesis are induced and controlled by a range heparan binding growth factors like members of the FGF and transforming growth factor beta families. Differentiation assays (FIG. 4) demonstrated that the addition of HS2 alone or in the presence of osteoinducive media (10 nM dexamethazone, 50 µM glycerophosphate and 100 µM L-ascorbate) or adipogenic media (DMEM with 10% FCS, 10 µg/ml insulin, 0.5 mM methlisobutylxanthine, 1 µM Dexamethasone) did not significantly effect on human mesenchymal stem cell differentiation, proving that although HS2 increases hMSC proliferation and preserves their "sternness", their capability to differentiate is not impaired.

Figure 5:
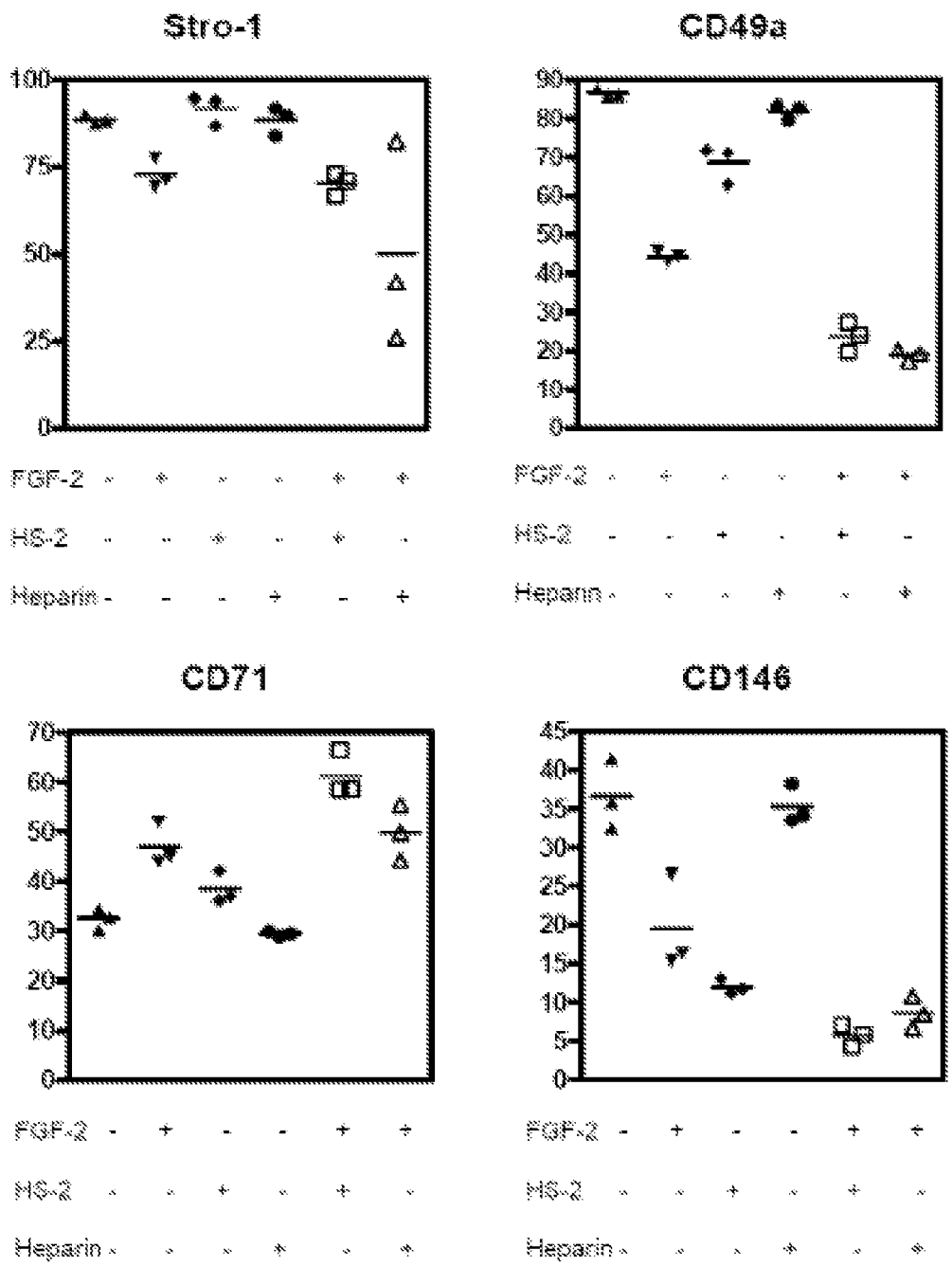
FIG. 5 illustrates the effect of heparan sulphate 2 on human mesenchymal stem cell surface marker expression. hMSCs were plated at 3300 cells/cm$^2$ in 60 mm culture dishes (NUNC(TM)) and cultured for 5 days in the presence or absence of 160 ng/ml HS2, 160 ng/ml heparin (negative control), 10 ng/ml FGF-2 (positive control), FGF-2/Heparin and FGF-2/HS2 combinations before measuring the proportion of cells positive for cell surface markers Stro-1 (A), CD49a (B), CD71 (C) and CD146(D) by antibody staining based flow cytometry. Each point represents the average and data of triplicate experiments.

The results obtained with surface markers of the stem cells, and STRO-1 in particular (FIG. 5) suggest that HS2 helps maintaining a "stem-like" phenotype by increasing the proliferation of the most undifferentiated cells. FIG. 5 demonstrates that human mesenchymal stem cells cultured in the presence of HS2 proliferate while maintaining their pluripotency while those human mesenchymal stem cells cultured with FGF-2 are able to proliferate but the cells lose some of their pluripotency. The maintenance of the mutipotentiality of mesenchymal stem cells is indicated by high level of STRO-1 expression, whereas the enhanced proliferation of the stem cells is hinted at by higher level of CD71 expression which is an iron transporter and important for proliferation. Simultaneously, cell mobility is increased implicated by decreased expression level of cell adhesion molecules CD49a and CD146. From the results it appears that the HS2 mediated mechanism of proliferation may include FGF-independent signalling pathways.

Figure 8:
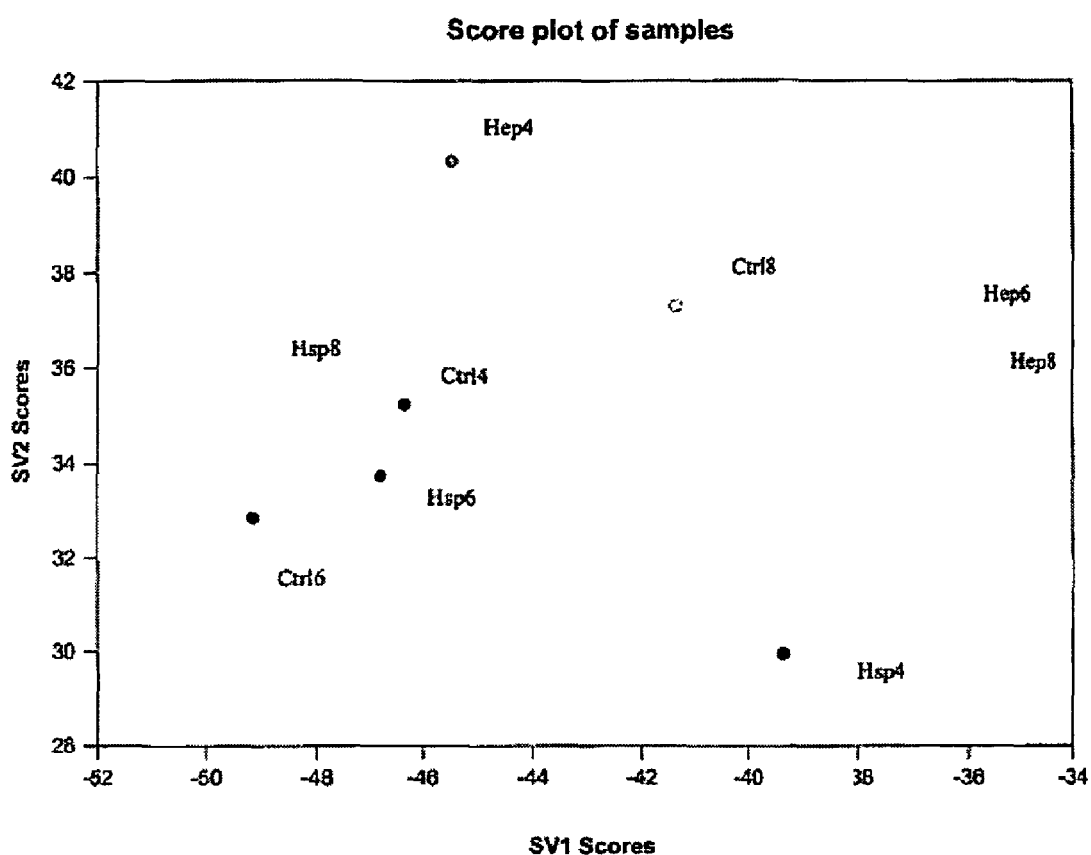
FIG. 8 illustrates the effect of heparan sulphate 2 on the multipotentiality of human mesenchymal stem cells. Gene expression signature was used to compare low and high population doublings (PD) cells cultured in different conditions (with or without 160 ng/ml HS2 or heparin). The signature was constructed using Singular Value Decomposition (SVD). SVD was performed on gene expression measurements from stem cell SuperArrays (extracted using GEArray, SuperArray Bioscience Corp, log-transformed and corrected for cross-chip variations), projecting the data onto the first 2 maximally-variant singular vectors. Abbreviations used: Hep heparin, Hsp heparan sulphate 2, Ctrl control. The numbers indicate the PD number.

Since there is no specific test to evaluate the stemness of mesenchymal stem cells beside their differentiative potential, gene expression signature was used to compare low and high PD cells cultured in the different conditions. The signature was constructed using Singular Value Decomposition (SVD) previously shown to be a powerful tool allowing the distinction between tumors subtypes based on gene profiling. As shown in FIG. 8, the high PD hMSCs cultured in the presence of HS2 (Hsp6 and Hsp8) strongly cluster with the low PD of the control (Ctrl4 and Ctrl6). However, the lowest PD hMSC treated with HS2 (Hsp4) sits on its own thus we can speculate that earlier passage of the control (whilst in the hands of Cambrex) would have clustered with it. These results are in accordance with the hypothesis that HS2 protects the "sternness" of the hMSC throughout population doublings. As for the cells treated with heparin (Hep4, Hep6, Hep8), they do not group with any others suggesting that the treatment profoundly altered their stemness and this should be reflected in the differentiation assays.

EXAMPLE 2

Therapies that seek to utilize adult human mesenchymal stem cells (hMSCs) are hampered by insufficient cell number with current ex vivo expansion methodologies leading to a loss of multipotentiality. Here we show that exogenous application of embryonic heparan sulfate sugar (HS-2) not only doubles the initial recovery of hMSCs from a bone marrow aspirate, but also increases the number of multipotent hMSCs by up to 13-fold during long-term expansion. Moreover, HS-2 acts to amplify a subpopulation of hMSCs harbouring longer telomeres and increased expression of the stem cell surface marker STRO-1. Gene profiling revealed that cells cultured in HS-2 possess a distinct signature that reflects their increased multipotentiality. Thus, HS-2 offers a novel means for decreasing the expansion time necessary for obtaining large numbers of mesenchymal stem cells without the addition of exogenous growth factors that compromise stem cell fate.

Materials and Methods

Cell Culture

Primary hMSCs and bone marrow mononuclear cells were isolated from three young healthy adult human donors (Cambrex). Cells were cultured in maintenance media (DMEM, 1,000 mg/l glucose, 10% FCS, Penicillin/streptomycin, 2 mM L-glutamine). For the different cell assays, cells were seeded at the following densities: proliferation assay (FIG. 9a): 1,000 cells/cm$^2$, viability assay (FIG. 9b): 3,300 cells/cm$^2$, BrdU incorporation (FIG. 9c): 21,000 cells/cm$^2$, cell cycle assay (FIG. 9d): 5,000 cells/cm$^2$ and long-term culture (FIG. 11a), cell surface marker expression (FIG. 10b-g and 11d) and RNA extraction for microarray: 5,000 cells/cm$^2$ at every time-point. Serum starvation was performed for 24 h in media with 0.2% FCS, pen/strep and L-glutamine. Media was changed every third day unless stated otherwise. For bone marrow mononuclear cell CFU-F assays (FIG. 10a) cells were seeded at 300,000 cells/cm$^2$ and for hMSC CFU-F assay (FIG. 11b) cells were seeded at 30 cells/cm$^2$.

Cell Assays

Cell counts, cell cycle and apoptosis assays were analyzed on a GUAVA PCA-96 benchtop flow cytometer following the manufacturer's instructions. Surface marker assays were analyzed on GUAVA PCA-96 and on a FACSArray flow cytometer (BD) (described elsewhere herein). For hMSC CFU-F assays, cells were seeded in 24-well plates in maintenance media and cultured for 12 to 14 days with a media change after one week. Cells were washed in PBS, fixed in methanol, dried, stained with 0.1% Giemsa in 50% methanol, washed again and dried. Colonies of more than 50 cells were counted. Bone marrow mononuclear cell CFU-F cultures were seeded in control or HS-2 containing media and cells were allowed to adhere for 3 days whereupon media was changed. Media was changed again after 7 days and at day 12 cells were trypsinized, counted and reseeded. After one additional passage, cells maintained in control or HS-2 containing media were analyzed for expression of surface markers. For the BrdU assay, cells were plated in 96-well plates and then serum-starved before the addition of media with or without (control) HS-2. BrdU incorporation was measured using the Cell Proliferation ELISA kit (Roche) following the manufacturer's instructions. The cells were pulsed with BrdU for 2 h at the time points indicated. Cloning assays were performed on cells expanded in HS-2 or control media. Single cells were seeded in 96-well plates using a FACSAria (BD Bioscience) and cultured for 14 days where wells with visible colonies (>50 cells) were counted. The same number of colonies from each culture was trypsinized, expanded and plated for multi-lineage differentiation in 12- and 24-well plates for adipogenesis and osteogenesis and in pellet cultures for chondrogenesis.

Telomere Length Assay

Figure 22:
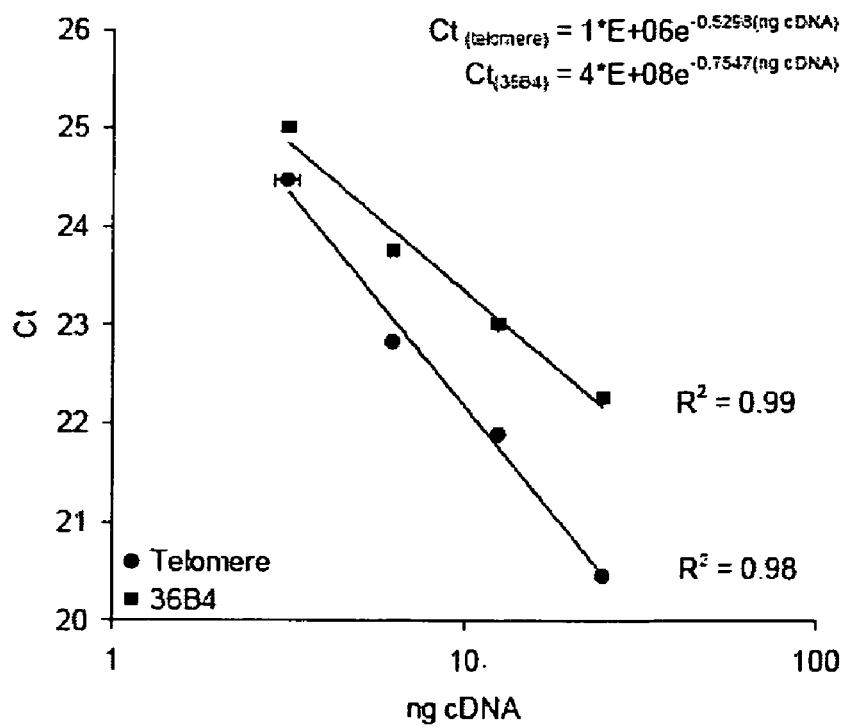
FIG. 22. Standard curve for relative quantification of telomere length in hMSCs. Chromosomal DNA from a confluent layer of human embryonic stem cell line BG01V (ATCC) was quantified. Serial dilutions of BG01V cDNA was analyzed for amplification of 36B4 (■) and telomere repeats (●) by RQ-PCR in triplicate and the amount of cDNA plotted as a function of the average Ct. The formulas for the trend lines shown in the figure were calculated by Excel and used to estimate the expression of 36B4 and telomere repeats in hMSCs expanded in HS2 or control media (FIG. 2b).

Chromosomal DNA was isolated from cells expanded in HS-2 or control media after the nominated population doublings. Cells were washed in PBS and lysed in buffer (10 mM Tris, pH 7.5, 10 mM EDTA, 10 mM NaCl, 1% SDS 0.05 mg/ml and RNase A (DNase free)) at 37° C. over night. Proteinase K (1 mg/ml) was added to the lysates which were incubated for 5 h at 37° C. DNA was precipitated with 2 vol. of absolute ethanol and 250 mM NaCl. Precipitates were washed in 70% ethanol, dried and resuspended in H$_2$O. DNA was quantified and 12.5 ng used for amplification of the 36B4 gene and telomeric repeats by RQ-PCR in triplicate, as previously reported[33,34]. The relative expression of telomeric repeats and 36B4 was estimated from (Ct vs. log quantity) standard curves made from chromosomal DNA isolated from the human embryonic stem cell line BG01V (FIG. 22).

Stem Cell Microarray

Total RNA was purified from control and HS-2 cultures after 21, 32 and 45 days in culture as above. Triplicate RNA samples were pooled (1:1:1 µg), labeled and used as probes on chemiluminescent cDNA arrays (GEArray S Series Human Stem Cell Gene Array; SuperArray Bioscience Corporation, Frederick, Md.). This procedure was repeated 3 times for each group at 21 days for a total of 3 triplicate pooled samples per group. Arrays were analyzed using a Chemi-Smart 3000 image acquisition system (Vilber Lourmat, Cedex, France). The construction of the signature based on SVD projection is described elsewhere herein.

Statistical Analysis

Figure 10:
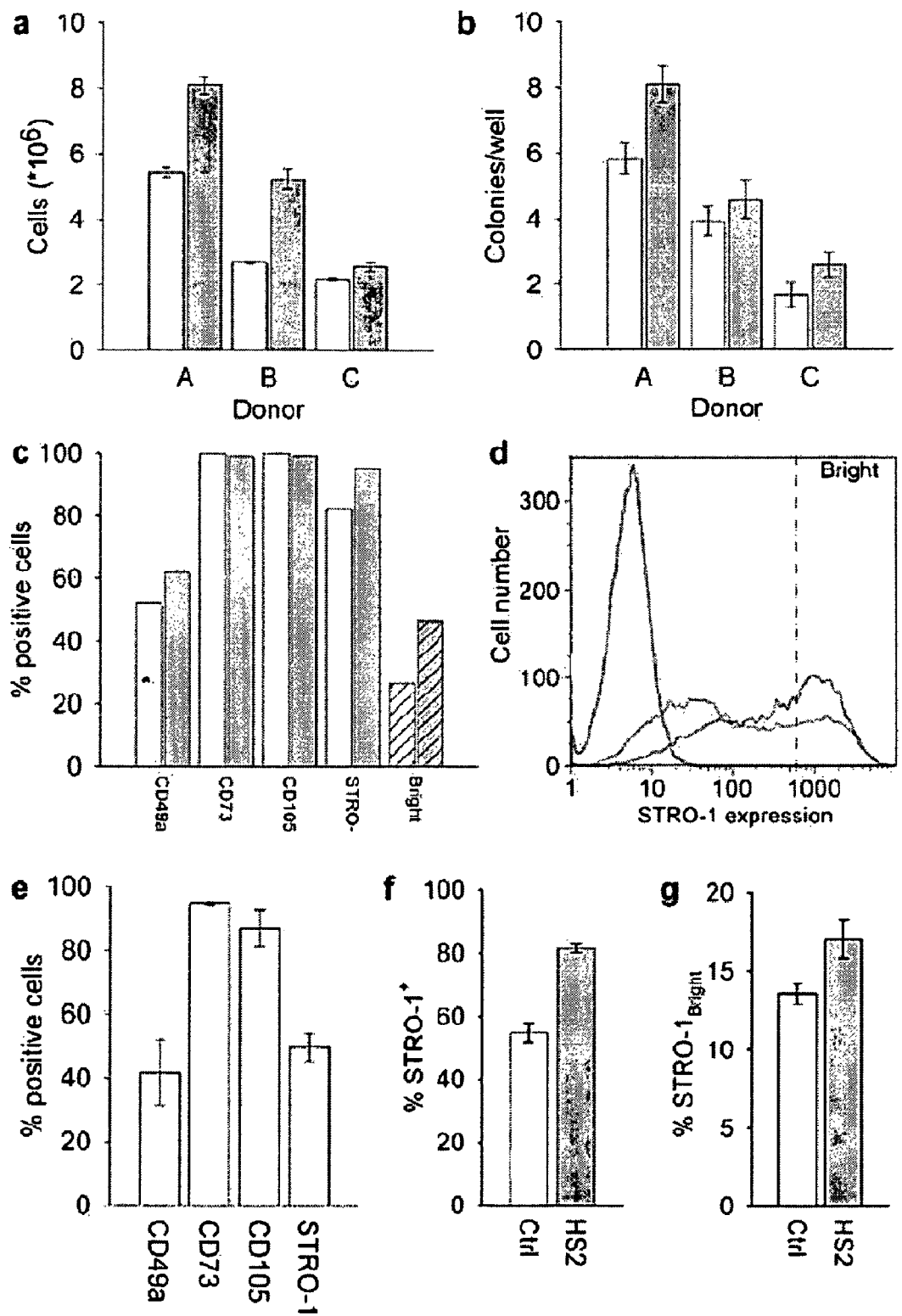
FIG. 10. Exposure to HS-2 increases the recovery of CFU-F hMSCs from bone marrow aspirates and stimulates expansion of the STRO-1 positive subpopulation.
 (a) Recovery of primary CFU-F hMSCs from 3 different bone marrow mononuclear cell donor batches in control or HS-2 containing media and
 (b) The number of colonies from 1:15 diluted cultures in control and HS-2 containing media.
 (c) Representative example of surface marker expression in CFU-F hMSCs recovered in control or HS-2-containing media.
 (d) STRO-1 expression profile of CFU-F hMSCs recovered in control or HS-2 containing media.
 (e) Expression of surface markers in established low passage hMSCs.
 (f) STRO-1 expression profile of low passage hMSCs cultured in control or HS-2 containing media for 7 days.
 (g) Quantification of STRO-1$^+_{bright}$.
Control is represented by white columns and HS-2 by grey columns. Isotype control is indicated by red line in c and e.
Figure 11:
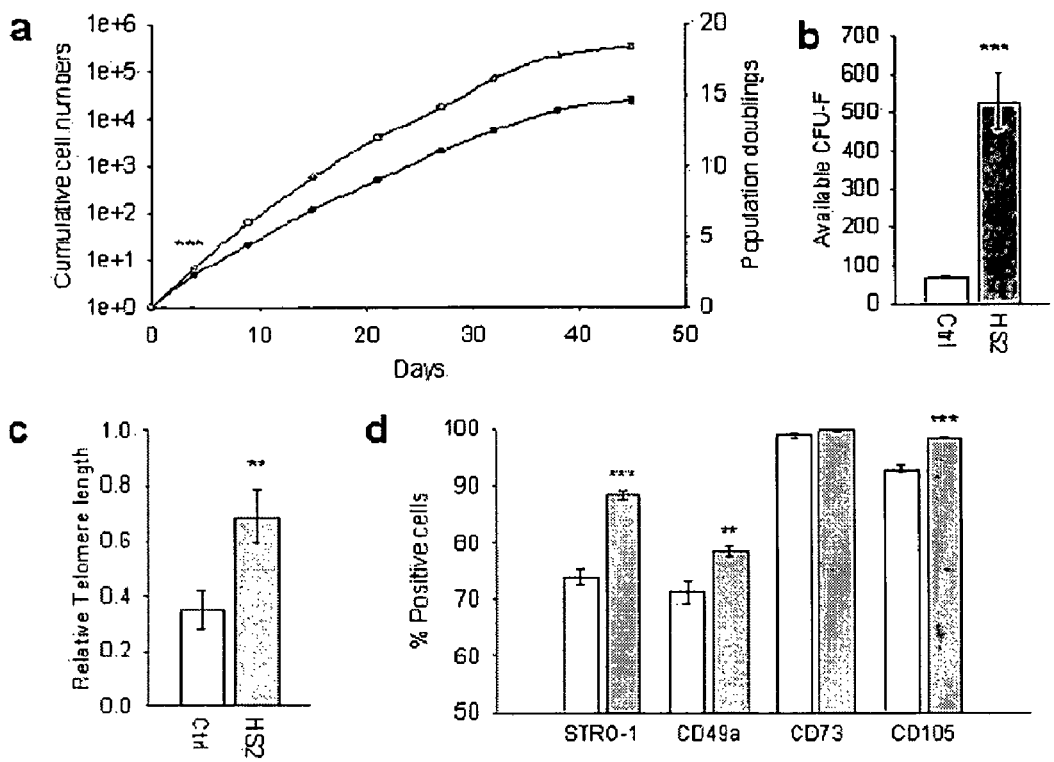
FIG. 11. Presence of HS-2 enriches for a subpopulation of more naïve stem cells with longer telomeres during large-scale expansion of hMSCs.
 (a) hMSCs were expanded in control or HS-2 media for 45 days and the cumulative number of cells produced by a single cell plotted against time.
 (b) Number of available CFUs after 21 days in culture.
 (c) Average telomere length of hMSCs expanded in control or HS-2 for 15 population doublings. The values are normalized to the length of telomeres in the original primary hMSC cultures (FIG. 22).
 (d) Expression of surface markers in cultures expanded for 40 days in control or HS-2 containing media.
Control is represented by black circles or white column and HS-2 is represented by white circles or grey column.

For each experiment the error bars in the figures represent the average and standard deviation of at least three independent cultures each measured in triplicate. FIGS. 10, 11 and 13 are representative results from experiments with all three pools of hMSCs. Significant differences between the control and HS-2 groups are marked with a single (p<0.05, t-test), double (p<0.005, t-test) or triple asterisk (p<0.0001, t-test). Quantitative differences between HS-2 and control were analyzed by an unpaired Student t-test assuming the null hypothesis using the web-based software available at http://www-.physics.csbsiu.edu/stats/t-test_bulk_form.html.

Cell Assays using a GUAVA PCA-96 Benchtop Flow Cytometer

At every passage, and during proliferation assays, cell numbers were determined using the Viacount FLEX reagent and software (Guava Technologies). For analysis of surface markers, cells were trypsinized, blocked for 1 h (PBS, 5% FCS, 1% BSA and 10% human serum), resuspended in staining buffer (PBS, 2% FCS, 0.02% NaN$_3$) and incubated with mouse anti-STRO-1 (R&D Systems) or mouse IgM control (Caltag) followed by PE-conjugated goat anti mouse-IgM (Caltag) or with PE-conjugated mouse anti human CD49a, CD73, CD105 (all BD bioscience) and an IgG control (Caltag). Cells were then analyzed from 2000 events using the Guava software. For cell cycle analysis, the cells were serum-starved and the media changed as previously described, then trypsinized after the time points mentioned, washed twice in PBS/1 mM EDTA, fixed in ice cold methanol and stored at 4° C. until staining. Fixed cells were washed once in staining buffer (see above), stained in a BD RNaseA/PI staining solution (BD Bioscience) and analyzed using the Guava software. For apoptosis assays, cells were cultured for 8 days before the expression of annexin and AAD-7 were measured using the Guava software.

Differentiation Assays

For adipogenic differentiation, cells were seeded (18,000 cells/cm$^2$) in 12-well plates and cultured to confluence at which time media was changed to adipocyte maintenance media (4,500 mg/l glucose) with or without (control) 1 µM dexamethazone, 10 µM insulin, 20 µM indomethazine and 115 µg/ml 3-isobutyl-1-methylxanthine and cultured for 28 days and stained with oil-red-O. For osteogenic differentiation, cells were seeded (3,000 cells/cm²) in 12-well plates for 24 h, then changed into maintenance media with or without (control) 10 nM dexamethazone, 10 mM β-glycerol-phosphate and 25 µg/ml Lascorbate-2-phosphate, cultured for 28 days and stained with alizarin red or alkaline phosphatase. For chondrogenic differentiation, cells (250,000 cells/tube) were pelleted in chondrogenic media (Cambrex) with or without (control) 10 ng/ml TGF-β3 in 15 ml tubes and cultured for 28 days where cells were fixed, embedded, mounted and stained with H&E and alcian blue. For all differentiation experiments, total RNA was isolated at day 28 and lineage specific gene expression analyzed by quantitative PCR.

Staining and Histology

Oil-Red-O staining of triglyceride; cells were washed in PBS and fixed in 4% paraformaldehyde (PFA) (Sigma) in PBS for 1 h, washed in water, stained with 3.6 µg/ml Oil-Red-O (Sigma) in 60% isopropanol for 1 h and washed in water. Alizarin Red staining; cells were washed in PBS, fixed in 4% PFA for 10 min, washed and stained for 30 min in 0.37% alizarin red (Sigma), pH 4.1, washed again and air-dried. Alkaline phosphatase staining was performed using the leukocyte alkaline phosphatase kit (Sigma) following the manufacturer's instructions. Chondrocyte pellets were washed in PBS and fixed in 4% PFA, embedded in O.C.T. and mounted onto glass slides. Fixed and mounted chondrocyte slides were stained with H&E and alcian blue. Stained cells were analyzed on an Olympus BX51 microscope.

RNA Purification and Relative-quantitative-PCR

Total RNA from carry-on cultures, adipocytes and osteoblasts were purified using a Nucleospin II kit (Macherey-Nagel). Chondrocyte pellets were washed with PBS, treated with collagenase II & IV, collected by centrifugation, resuspended in Trizol (Invitrogen) and the RNA isolated. RNA quality and concentration was assessed and 0.5 µg used for reverse transcription using Superscript III polymerase (Invitrogen) as per the manufacturer's recommendations. Table 1 (FIG. 27) shows the Taqman primer/probes used for quantitative PCR. Primers and probes were designed using Primer express (Applied Biosystems) and synthesized by Proligo. Probe sequences were modified to dual labelled LNA (FAM/BHQ-1) hybridization probes, (in the table upper case letters in the probe sequences shows LNA nucleotides). Dual labeled MGB (VIC/TAMRA) labeled 18S rRNA primer probes were used as control for all reactions. All PCR reaction products were analyzed by agarose gel electrophoresis and sequenced to verify the specificity of the amplicon. Each quantitative PCR reaction (20 µl total) contained 80 ng cDNA, 300 mM forward and reverse primer, 250 µM probe (100 µM Collagen2a1 probe was the only exception) and 10 µl Taqman Universal master mix (Applied Biosystems). Detection of 18S rRNA was performed in a similar way using 50 nM forward and 50 nM reverse primer and 100 nM probe. Quantitative PCR reactions were performed in triplicates on an ABI Prism 7000 sequence detection system (Applied biosystems), with an initial 10 min activation step at 95° C. followed by 45 cycles of 95° C. for 20 sec; 55° C. for 10 sec. 60° C. for 30 sec and 72° C. for 40 sec. Relative expression units were calculated by normalizing the 2(-DCt) values of the gene to the 2(-DCt) values of 18S and multiplied by 106.

Singular Value Decomposition (SVD)

This forms the basis for a linear projection of a dataset onto a new reduced dimensional space that captures the maximum information present in the original data (that is, a principal components analysis).

We have used SVD as a means of processing and analysing gene expression data to determine and compare the retention of stemness of cultured stem cells. SVD analysis shows that cells cultured in HS, including HS-2, retain their stemness for longer culture times.

Locally-Weighted Regression (LOESS) Normalization for Stem Cell Array Data

Intensity measurements which are derived from gene hybridization-based technologies are often subject to variations across the gene chips that prevent meaningful comparisons of individual genes. These cross-chip variations necessitated adjustments of the chip intensities to a common distribution. A widely used alternative to scaling intensities by a constant global difference in hybridization is to fit an additive linear-model to the log-transformed gene intensity values using a LOESS smoothing function[39]. The fitted intensities are then used to infer differential expression.

Figure 28:
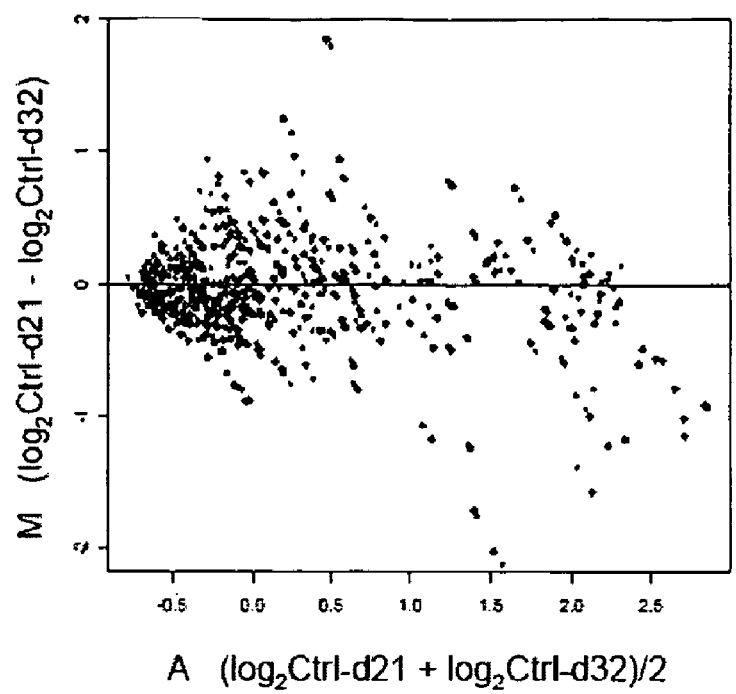
FIG. 28. MA plot after locally-weighted smoothing. Only data for Ctrl-d32 vs Ctrl-d21 is plotted. Intensities have been log-transformed and median scaled. Data before smoothing is depicted in blue and fitted values are in red.
Figure 29:
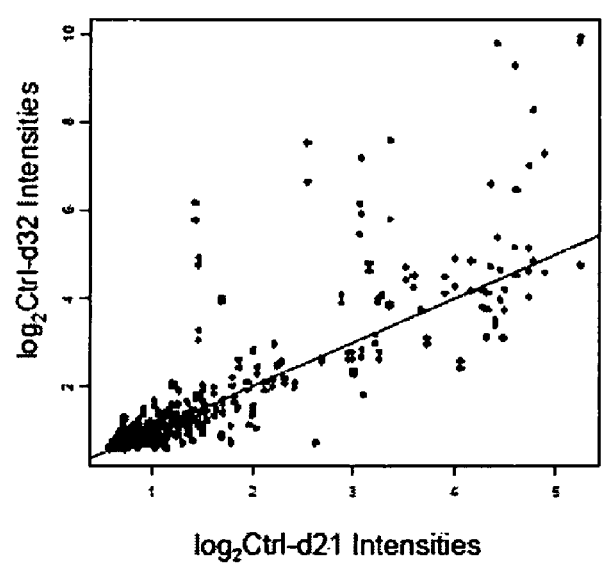
FIG. 29. Data plots after locally-weighted smoothing. Data colored as in FIG. 28.

We first examined the effects of varying the neighborhood parameter, α, on the smoothing function through comparisons between controls. No radical shifts in the curvature of data plots were observed for ranges of $0.2 \leq \alpha \leq 0.8$ (data not shown). A conservative value, $\alpha = 0.2$, was then selected and applied to all arrays. MA plots reveal only a moderate degree of shift in the plot (See FIG. 28 for Ctrl-d21 vs Ctrl-d32) with effects that are more pronounced for extreme values of differential expression (See FIG. 29).

Singular Value Decomposition of Stem Cell Array Data

The gene expression microarray data used in these experiments are high-dimensional datasets involving hundreds of genes and their co-expressions. Despite this seeming complexity, most of the important molecular information differentiating between HS-2 and controls actually exist as a number of simple and fundamental patterns. We wish to discover the most informative patterns (or singular vectors) within the dataset and use them to derive robust definitions for the effects of HS-2 on stemness through singular value decomposition.

A matrix, A, which represents stem cell array data consisting of m separate experimental conditions (treatments of heparan sulfate vs controls) on the rows and n variables (genes on each array) on the columns is first pre-processed by taking its covariance matrix prior to singular value decomposition[40]. The matrix is decomposed as follows:

$$A_{(n \times n)} = U_{(n \times n)} S_{(n \times n)} V'_{(n \times n)} \quad (1)$$

where S is a diagonal matrix consisting of the singular values $(\lambda_1, \lambda_2 \ldots \lambda_n)$ of matrix A'A (A' denotes the transpose of A). The columns of U and V are respectively the singular vectors corresponding to the matrices A'A and AA'. Both U and V are orthogonal matrices so that projections, C, onto these vectors is given as follows:

$$C = USV'V = AV = US \quad (2)$$

The proportion of variance associated with the first t vectors, $Var_t$, is therefore given by:

$$Var_t = \frac{\sum_{i=1}^{t} \lambda_i}{\sum_{i=1}^{n} \lambda_i} \qquad (3)$$

Each singular value therefore represents the amount of variation associated with each singular vector (sets of genes) that distinguishes between the samples. Each component of the singular vector, the factor loadings, are therefore an expression of the importance of each gene in the distinction:

$$p_{ij} = v_{ij} \qquad (4)$$

Where $p_{ij}$ is the contribution of the ith gene to the j-th component and $v_{ij}$ is the i-th component of the j-th singular vector.

Figure 32:
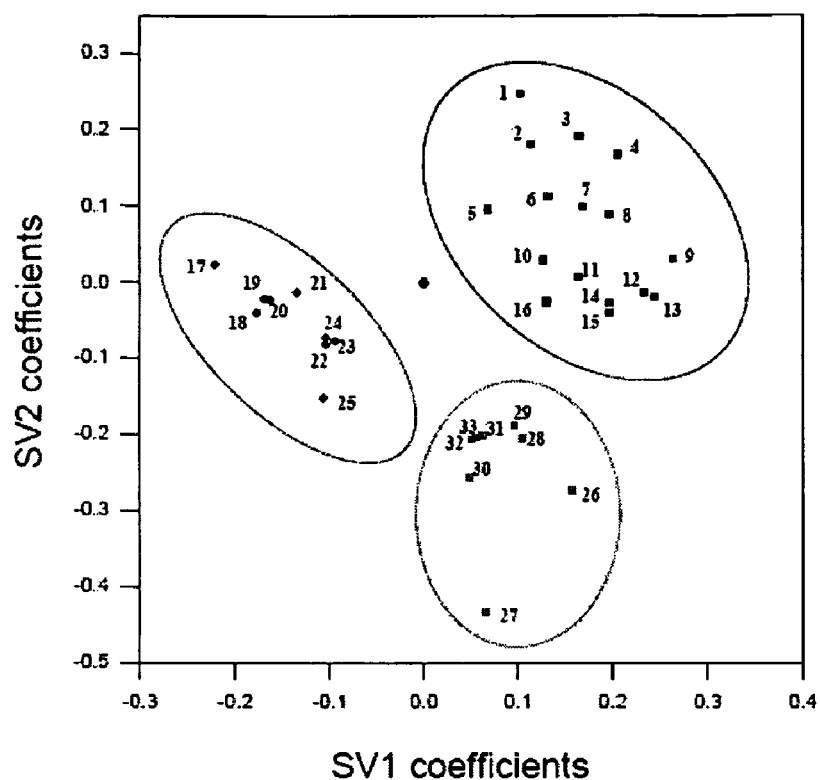
FIG. 32. Gene selection based on coefficients of singular vectors. Filtering of coefficients was based on a 90-th percentile of Euclidean distance from the origin (black cross). Clusters denote angles subtended by genes of each cluster with respect to the x-axis. They are colored blue (cluster 1—top right), red (cluster 2—middle left) and green (cluster 3—lower middle) and enclosed in ellipses. Genes are numbered as in Table 2 (FIGS. 30 and 31).

Previous research has shown that genes with the highest factor loadings (Table 2) are greatly distanced from the origin and share similar characteristics in 2-D loading plots (see FIG. 32). Several groups of potential stemness markers were defined based on positions in the loading plot. We examined the efficacy of using the top 90th-percentile distant genes by reconstructing the SVD using only these genes. The score plot revealed a clear separation of HS-2 and control in all 3 samples (see FIG. 33). These results support the usefulness of SVD for separation and classification of samples.

Stability of SVD Projection Scores Assessed by Statistical Resampling

In addition to defining markers for stemness, we performed an additional validation of the SVD technique through statistical resampling. This is to evaluate the robustness of stemness signatures and clustering effects based on SVD scores. A natural criterion for the distance between any pair of samples, $C_a, C_b \in R^P$ under an SVD projection on the first P singular vectors is given by the following Euclidean metric in $R^P$:

$$\|L\|_p = \left(\sum_{i=1}^{P} |C_{ai} - C_{bi}|^p\right)^{1/p} \qquad (5)$$

This metric avoids errors produced by arbitrary changes in the sign of eigenvectors of any particular axes resulting from axis reflections when raw projection scores are used[41]. As the Eigen values of the first 2 singular vectors constitute approximately 70% of variance, we have chosen P=2.

Gene expression measurements may often be affected by errors introduced during capture of luminence intensities leading to an artificial inflation or deflation of individual intensity values in a non-systematic fashion. To determine the significance of clustering effects for the various treatment conditions under an SVD projection and their effects on stemness therefore requires the derivation of a statistical framework for estimation of variance in projection scores in the presence of outliers. We formally modeled this variation (rather than base comparisons against randomly-generated data[42]) through the use of a non-parametric bootstrap[43]. The method more accurately approximates parameters of interest, is tolerant of violations of normality and equivariance assumptions in real data that adversely affect other parametric multivariate approaches and has therefore been found suitable for application under diverse contexts in gene expression[7,8].

Following an established procedure[9], given A, we construct A* by drawing with replacement the $a_i^*$, computing (5) for a total of B iterations. Given the computationally intensive nature of the SVD, we have chosen B=1000.

Figures 34, 35:
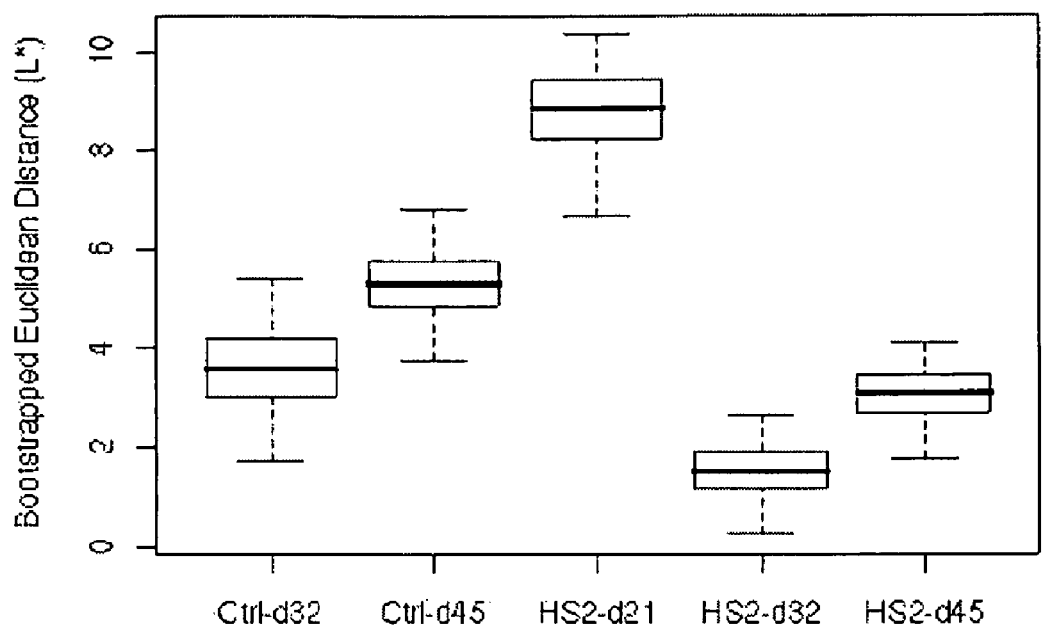
FIG. 34. Bootstrapped Euclidean distances between sample projection scores. Distributions were approximately normal (median distances at centre of upper and lower quartiles). Dashes denote adjacent values located interquartile distant from upper and lower quartiles. Only comparisons with respect to Ctrl-d21 are shown. HS distances of later passages were essentially non-overlapping with respect to control distances.
FIG. 35. Table 3—Table of bootstrap statistics. [a]Euclidean distance estimates were based on first 2 singular vectors. [b]Lower CL and [c]Upper CL provide 95% confidence limits estimated within 1000 bootstrap replicates.

A parallel boxplot of the distribution of L* for each sample with respect to Ctrl-d21 shows an approximate normal distribution (FIG. 34). We derived estimates of the percentiles of a Student's t-statistic for each pair of distances, T*, as follows[10]:

$$T^* = \frac{L^* - \hat{L}}{\hat{\sigma}^*} \qquad (6)$$

Where $\hat{L}$, $\hat{\sigma}$, $L^*$ and $\sigma^*$ are the observed values of L, its standard error, a bootstrap estimate of L and its corresponding bootstrap standard error estimate respectively. The percentiles, $T^{*(0.95)}$ and $T^{*(0.05)}$ therefore give the bootstrap-t approximate confidence intervals:

$$L \in [\hat{L} - \hat{\sigma} T^{*(0.95)}, \hat{L} - \hat{\sigma} T^{*(0.05)}] \qquad (7)$$

Bootstrapped confidence estimates for L are listed in FIG. 35. All mathematical computations were implemented in MATLAB (Mathworks Inc, Natick, Mass.) and R (www.r-proiect.org). HS2-d32 or even HS2-d45 bootstrap intervals are much smaller with respect to Ctrl-d21 than any other treatments. The results indicate that clustering effects on SVD scores are robust even in the presence of noise. Overall, this supports the notion that the clustering of HS-2 samples with controls of earlier passages indicates an effect of HS-2 treatments on preservation of stem ness.

Results

Figure 9:
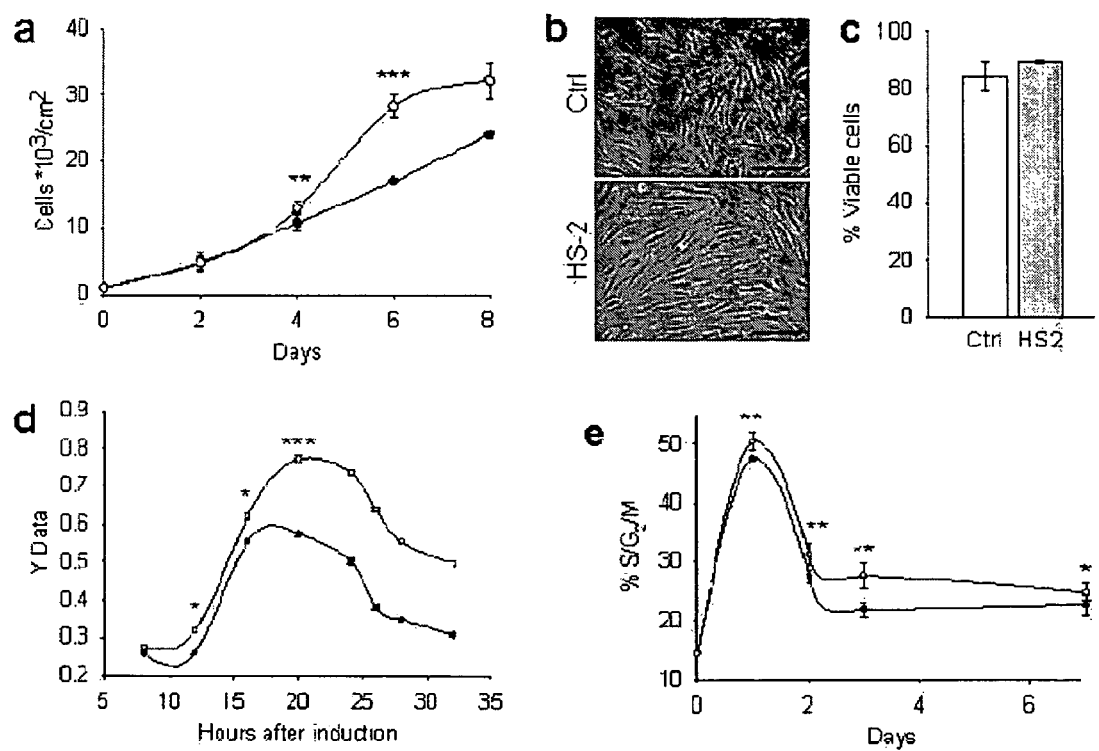
FIG. 9. Short-term exposure to HS-2 increases the proliferation of hMSCs.
 (a) Proliferation of cells exposed to 160 ng/ml of HS-2.
 (b) Phase contrast micrograph of cells cultured in control (top) and HS-2 containing media (bottom), bar=200 µm.
 (c) Viability levels after 8 days exposure to HS-2.
 (d) Incorporation of BrdU during short-term exposure to control or HS-2
 (e) Proportion of cells in S/G2/M phases of the cell cycle when cultured in HS-2. Control is represented by black circles or white column and HS-2 is represented by white circles or grey column.
Figure 20:
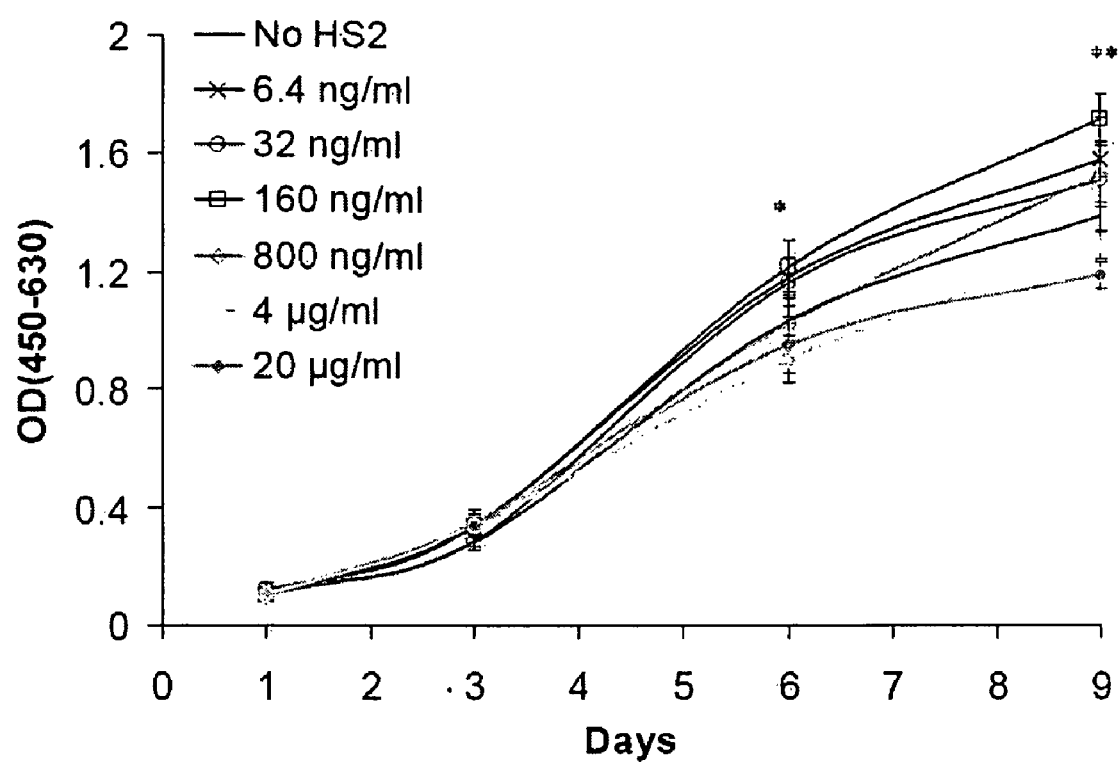
FIG. 20. HS-2 increases hMSC metabolic activity in a dose-dependent manner. hMSCs were plated at 3300 cells/cm2 in 96-well plates and cultured in the presence of 0, 6.4, 32, 160, 800, 4,000 or 20,000 ng/ml HS-2. Metabolic activity was determined using the WST-1 assay (Roche) after 1, 3, 6 and 9 days. All measurements were performed in triplicate; the graph shows the average and standard deviation of a representative experiment. Significant differences between the control and 160 ng/ml HS-2 group is marked with a single ($p<0.05$, t-test) or double asterisk ($p<0.005$, t-test).

One mitogen that has been shown to be a powerful driver of proliferation for both embryonic and adult stem cells is FGF-2[14,15,17,18,25] the activity of which is dependent on HS. We have previously purified an FGF-2-binding HS(HS-2)[26] free of core proteins and shown it has potent bioactivity towards neural precursor cells. Here we use it as a media supplement for the ex vivo expansion of hMSCs without the addition of exogenous growth factors and observed a consistent dose-dependent effect across several donors (FIG. 20). HS-2 (160 ng/ml) increased cell numbers over 6 days in sub-confluent monolayers by 65% (p<0.005), (FIG. 1a) and was associated with changes in cell size and morphology, with HS-2-treated cells appearing smaller, more elongated and more aligned (FIG. 1b). Exogenous addition of heparin, a heterogeneous and non-specific control HS GAG, also increased the proliferation of hMSCs, but to a much lesser extent than HS-2, while having no effect on cell morphology (data not shown). Notably, this effect was not due to increased viability (FIG. 9c); rather it was due to an increase in the number of cells entering the cell cycle, with a small proportion entering the cycle more quickly, thus creating a significant difference in the number of cells in S-phase after 24 h (FIG. 9d). Exposure to HS-2 maintained an increased cell cycle progression for up to 72 h compared to control media, which only stimulated cells for 24 h (FIG. 9e). Collectively these results indicate that HS-2 increases cell number by stimulating a population of normally quiescent cells to enter the cell cycle and sustained their proliferation for an extended period of time.

As the frequency of hMSCs in a bone marrow asiprate is extremely low, the recovery of adherent cells with multipotentiality (called colony forming unit-fibroblastic (CFU-F))[27] is critical. We seeded BMMNCs from three different donors in media supplemented with or without HS-2 and counted both adherent cell number and the number of colonies that had formed after 12 days. The number of adherent hMSCs varied between the three donors, but in all cases, exposure to HS-2 significantly increased the number of cells recovered (up to 2-fold compared to controls) (FIG. 10a). In addition we observed an increase in the number of CFU-Fs in the HS-2 treated cultures (FIG. 10b).

We further characterised the adherent hMSCs using specific cell surface antigen expression after one additional passage in either control or HS-2-containing media. Irrespective of treatment, none of the cells expressed the hematopoietic marker CD45, but strongly expressed the hMSC markers CD49a, CD73, CD105 and STRO-1 (FIG. 10c). It is known that the majority of the CFU-Fs derived from a BMMNC sample are contained within a subpopulation of hMSCs with high STRO-1 expression (the STRO-1$^{+bright}$ population)$^{9,28}$. Importantly, CFU-Fs derived from hMSCs cultured in HS-2 had a much higher proportion of STRO-1$^{+bright}$ cells compared to control conditions (representative data shown in FIGS. 10c & d). The increase in proliferation, coupled with the higher number of CFU-Fs, yielded almost 4-fold more STRO-1$^{+bright}$ cells.

To determine whether HS-2 preferentially expanded the STRO-1+hMSC population in short-term culture, we seeded hMSCs in either HS-2 or control media and analyzed the expression of CD49a, CD73, CD105 and STRO-1 after 7 days in culture (FIG. 10e). We found that HS-2 significantly increased the STRO-1$^+$ population (and notably the STRO-1$^{+bright}$ population) (FIGS. 10f & g), an effect that was absent in both control and heparin-treated cells (heparin data not shown). We also observed no difference in the expression of CD49a, CD73 and CD105 during short-term culture (data not shown). The results suggest that HS-2 not only enhances the proliferation of CFU-Fs during the initial stages of culturing, but also the subsequent expansion of the hMSCs and the expression of STRO-1.

Figure 21:
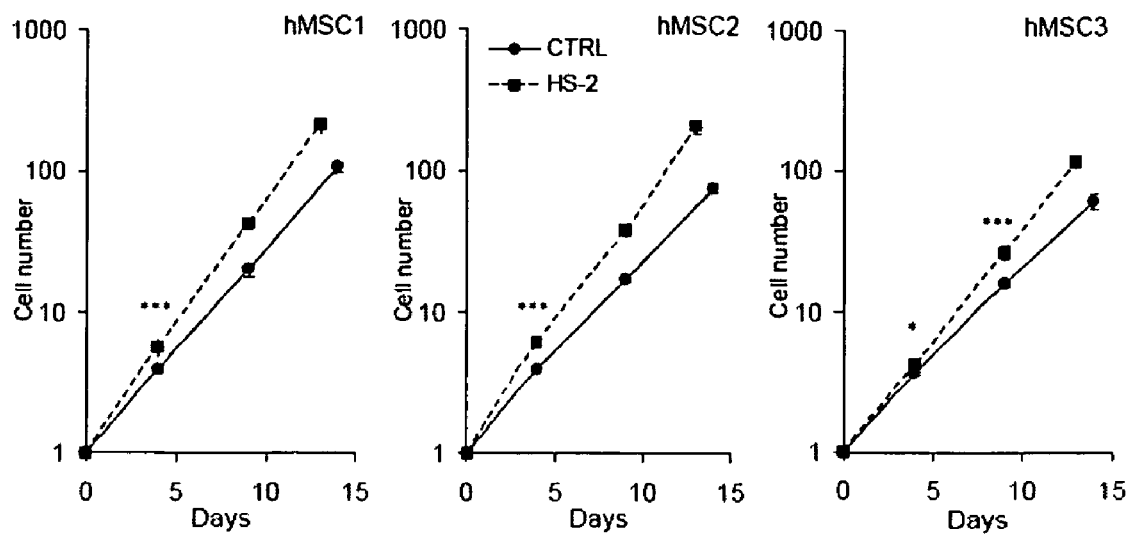
FIG. 21. HS-2 increases the number of population doublings in the three different pools of hMSCs. Graph represents the cumulative cell number of cells during the culture period for three different pools of hMSCs. Low passage hMSCs were plated at 5000 cells/cm² and cultured in media with or without 160 ng/ml HS-2 to sub-confluence, whereupon cells were trypsinized, counted and reseeded at 5000 cells/cm² in the respective media. This was repeated for a period of two weeks. Numbers in the graph are cumulative increases in cell number starting from one cell. Significant differences between the control and HS-2 group is marked with a single ($p<0.05$, t-test) or triple asterisk ($p<0.0001$, t-test).

Expansion of hMSCs for therapeutic use typically requires cells to be cultured for up to one month, so yielding ~10,000-fold increase in their number. By way of comparison, we expanded hMSCs in HS-2 or control conditions following established protocols and conditions (Osiris and Cambrex). The HS-2 cultures produced nearly an order of magnitude more hMSCs than controls after only 21 days (FIG. 11a). Similar expansion was observed for hMSCs from three separate donors, thus demonstrating the effect was not donor-specific (FIG. 21).

Figure 23:
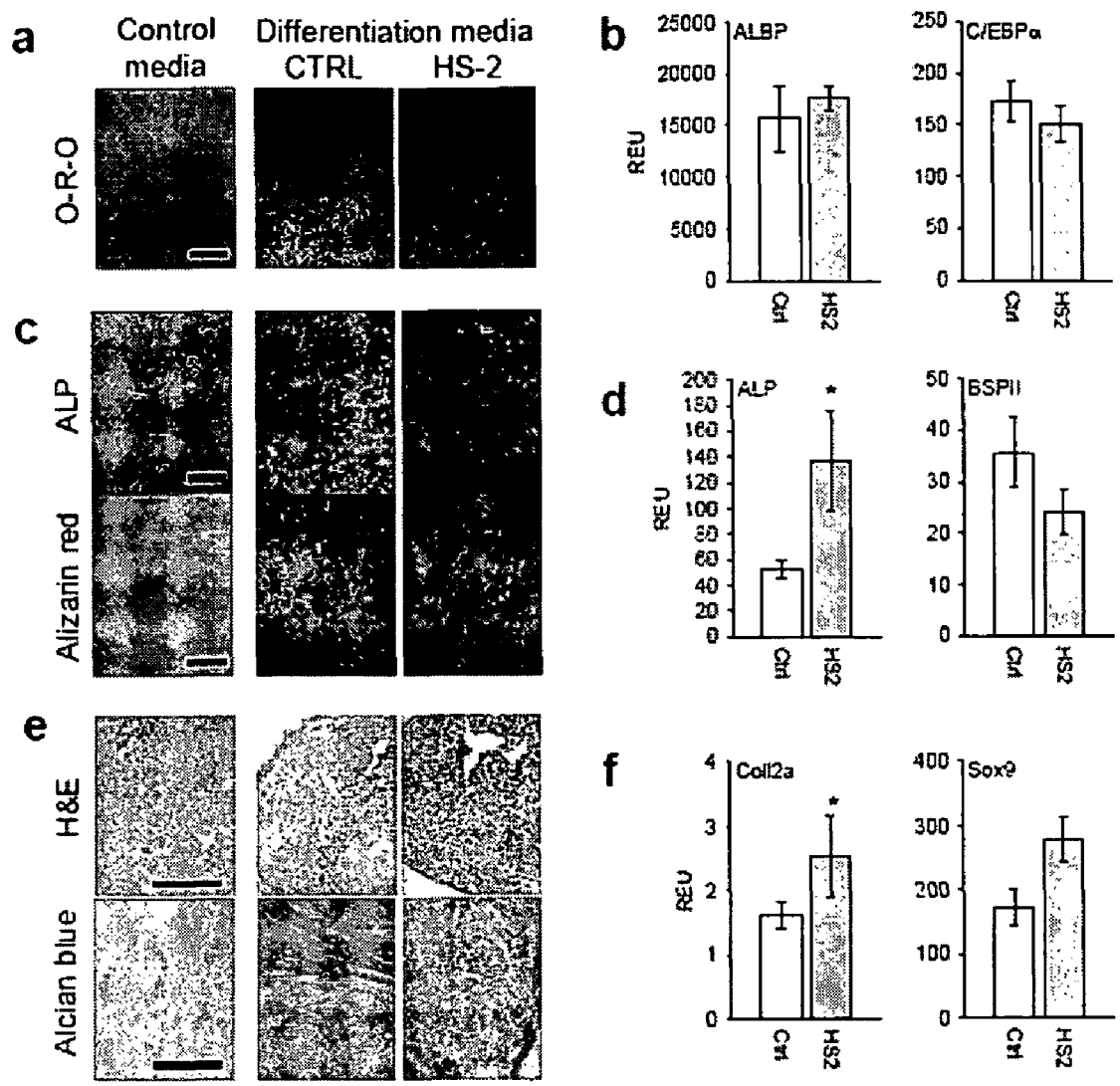
FIG. 23. Long-term cultures of hMSCs in media containing HS-2 maintains their multipotency. Differentiative potential of hMSCs expanded in control (white) or HS-2 (grey) media for 38 days as in FIG. 3a. Expanded cells were differentiated for 28 days in adipogenic, osteogenic or chondrogenic media. Adipogenesis was measured by (a), Oil-Red-O staining (Scale bar=1 mm) and (b) quantitative PCR, Osteogenesis was measured by (c) alkaline phosphatase, alizarin red (Scale bar=1 mm) and (d) quantitative PCR, and Chondrogenesis was measured by (e) H&E and alcian blue staining (Scale bar=500 μm) and (f) quantitative PCR. CCAAT/enhancer binding protein-α (C/EBPa), adipocyte lipid binding protein (ALBP), alkaline phosphatase (ALP), bone sialoprotein 2 (BSPII), Collagen2a1 (CoII2a) and SOX9.

To ensure that hMSCs expanded in HS-2 retained their stem cell-like characteristics we analysed the proportion of CFU-Fs in limited dilution assays, the average telomere length of the expanded hMSCs, multilineage potentiality and the specific cell surface antigen expression of the hMSC markers CD49a, CD73, CD105 and STRO-1. Regardless of the culture conditions, hMSCs cultured for 21 days had a similar proportion of CFU-Fs (about 7% for HS-2, data not shown). Thus, even though HS-2 cultures had undergone more than three additional population doublings (PDs) compared to the control (FIG. 11a), they maintained their proportions of CFU-Fs, thereby yielding an 8-fold increase in available CFU-Fs (FIG. 11b). Next we measured the average telomere length and found that cells expanded for 15 PDs in HS-2 had significantly longer telomeres than cell expanded for 15 PDs in control media (FIG. 11c). We also verified if any residual telomerase activity was present, but as previously shown$^{11,12}$, no telomerase activity could be detected in these cells irrespective of the culture treatments (data not shown). To test whether prolonged exposure to HS-2 adversely affected the hMSC phenotype, we analyzed surface marker expression and multilineage differentiation after 45 and 38 days expansion respectively. Notably, the expression of STRO-1, CD49a, CD105 increased, whereas CD73 was unaffected, indicating a maintenance of their phenotype (FIG. 1d). This correlated with the results of the adipogenic, osteogenic and chondrogenic assays in which hMSCs expanded in HS-2 showed similar and in some cases increased multipotentiality compared to control (FIG. 23). Importantly however, when hMSCs were induced to differentiate in the presence of HS-2, it had no adverse effect, in contrast to cells exposed to FGF-2 that failed to differentiate (FIGS. 24 and 25). Overall these results indicate that HS-2 is able to significantly increase the proliferation of a subpopulation of multipotent hMSCs that have significantly longer telomeres and a greater expression of cell surface antigens that are characteristic of hMSCs. Furthermore, the use of HS-2 for such expansion decreased culture time from 36 to 24 days (FIG. 11a), a significant reduction with potential impact on the therapeutic utility of the stem cells.

Figure 12:
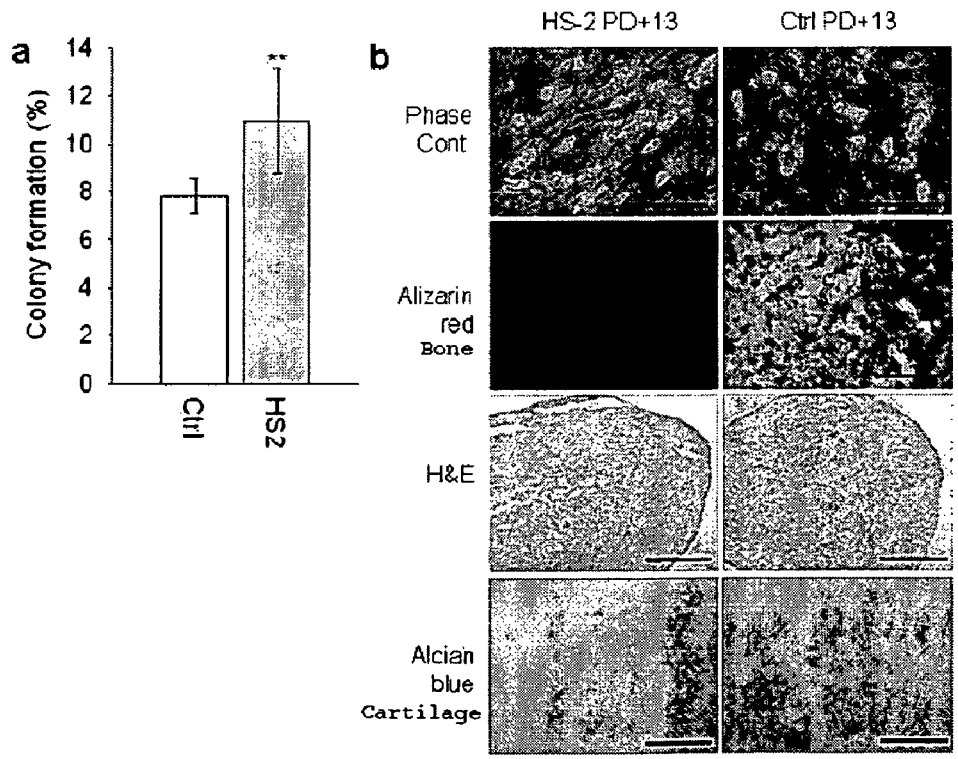
FIG. 12. HS-2 expands hMSCs that are able to clone and undergo multilineage differentiation.
(a) Single cell colony formation of cells expanded in HS-2 or control media. Cloning frequency of cells expanded for 13 PDs in HS-2 or control media.
(b) Multilineage differentiation assay of representative clones from cultures expanded for 13 PDs in control or HS-2 media. Phase contrast micrographs of lipid containing cells from adipogenic cultures, alizarin red staining of mineralizing osteogenic cultures and H&E and alcian blue staining of chondrogenic cultures (Scale bars=200 μm).

As there is an inverse relationship between time in culture and maintenance of stem cell-like characteristics, we evaluated the multipotentiality of single cell clones isolated from hMSCs expanded for 13 PDs in HS-2 or control media. Single cells were seeded into 96 multi-well plates and cultured for 2 weeks. The cells originally expanded in HS-2 showed significantly higher colony formation (38%) than cells expanded in control media (FIG. 12a). The cloning frequencies observed in our early CFU-F assays (7%, FIG. 11b) and the cloning assay from carry-on cultures of hMSCs (12%, FIG. 12a) are comparable to the previously reported frequencies obtained by enrichment of hMSCs after STRO-1 sorting. Such sorting results in a CFU-F frequencies below 1%, whereas the STRO-1$^{bright}$ population yields a frequency of 9%$^{13,35}$. The colonies here were expanded and assessed for adipogenic (lipid accumulation), osteogenic (alizarin red staining) and chondrogenic (alcian blue staining) differentiation potential (FIG. 12b). RQ-PCR analysis of adipocyte lipid-binding protein (ALBP) and alkaline phosphatase (ALP) expression was also used to confirm adipogenesis and osteogenesis respectively (data not shown). More than half (57%) of the HS-2 expanded colonies were able to undergo multilineage differentiation with the remaining colonies (43%) restricted to the osteogenic lineage. In contrast, control-expanded colonies were unable to undergo chondrogenesis, with the majority (71%) restricted to the osteogenic lineage. Cells expanded for 17 PDs in HS-2-containing media showed a similar colony formation frequency as control cells expanded for 13 PDs (~8%), but when expanded and tested for differentiation, some of the PD 17 HS-2-expanded clones were still multipotent (33%) (data not shown). These data further confirm that the hMSCs expanded in the presence of HS-2 have significantly increased multipotentiality compared to control cells expanded for the same number of PDs. Thus, not only does the presence of HS-2 decrease the expansion time, it also markedly prevents the loss of multipotentiality observed in the control cultures at the point where they have reached therapeutic numbers.

Figure 33:
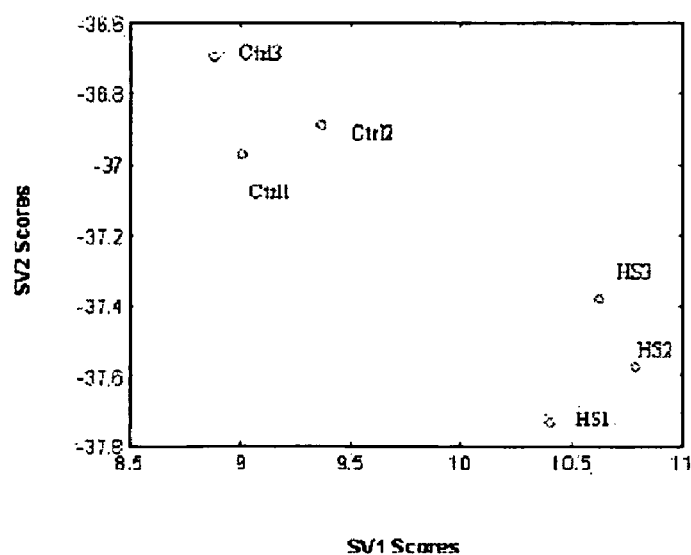
FIG. 33. Projection of the three hMSC patient pools after 21 days of culture in control, HS-2 containing media based on identified biomarkers. Controls (red circles; Ctrl) are distinguished from HS (green circles; HS). (Pool 1, 2 and 3, hMSC1, 2 and 3 respectively (FIG. 21).

At present there is no specific test to evaluate "stemness", so hMSCs are either assessed in vitro or in a mouse skin flank model. We therefore developed a robust assay to assess changes in stemness based on gene profiling. We used a commercial stem cell-specific gene array to create an expression signature by singular value decomposition (SVD)$^{29,30}$ and projected the data onto the first two maximally-variant singular vectors (FIG. 13). SVD has previously been used as a powerful tool to distinguish between tumour subtypes$^{31,32}$. Such an analysis showed that cells expanded in the presence of HS-2 for 21 days had a signature that was distinct from all the other samples, with clones isolated from this time-point having the best multipotentiality (FIG. 12), further reinforcing the hypothesis that HS-2 targets a naïve population of hMSCs. Furthermore, cells cultured for 32 and 45 days in the presence of HS-2 had signatures clustered with those from control media at day 21 and 32 respectively. Considering the fact that the signature of the control cells at day represents the least naïve cells, we can therefore conclude that cells treated with HS-2 for 45 days have a signature typical of younger cells. When the stem cell signature from two other donors was compared to the first, (FIG. 22), they clustered together on the basis of treatment (FIG. 33). This indicates that the effects of HS-2 is not donor-specific and that signatures produced by SVD can be used to reliably compare cells from different donors. Thus SVD analysis has the potential to be used for characterizing the sternness of cells prior to their therapeutic use.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by a preferred embodiment, modification and variation of the invention herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention.

Other embodiments are within the following claims.

References

1. Jiang, Y., et al. Pluripotency of mesenchymal stem cells derived from adult marrow. *Nature* 418, 41-49 (2002).
2. Horwitz, E. M., et al. Isolated allogeneic bone marrow-derived mesenchymal cells engraft and stimulate growth in children with osteogenesis imperfecta: Implications for cell therapy of bone. *Proc Natl Acad Sci USA* 99, 8932-8937 (2002).
3. Miyahara, Y., et al. Monolayered mesenchymal stem cells repair scarred myocardium after myocardial infarction. *Nat Med* 12, 459-465 (2006).
4. Petite, H., et al. Tissue-engineered bone regeneration. *Nat Biotechnol* 18, 959-963 (2000).
5. Quarto, R., et al. Repair of large bone defects with the use of autologous bone marrow stromal cells. *N Engl J Med* 344, 385-386 (2001).
6. Pittenger, M. F. & Martin, B. J. Mesenchymal stem cells and their potential as cardiac therapeutics. *Circ Res* 95, 9-20 (2004).
7. Le Blanc, K., et al. Treatment of severe acute graft-versus-host disease with third party haploidentical mesenchymal stem cells. *Lancet* 363, 1439-1441 (2004).
8. Stenderup, K., Justesen, J., Eriksen, E. F., Rattan, S. I. & Kassem, M. Number and proliferative capacity of osteogenic stem cells are maintained during aging and in patients with osteoporosis. *J Bone Miner Res* 16, 1120-1129 (2001).
9. Gronthos, S., et al. Molecular and cellular characterisation of highly purified stromal stem cells derived from human bone marrow. *J Cell Sci* 116, 1827-1835 (2003).
10. Digirolamo, C. M., et al. Propagation and senescence of human marrow stromal cells in culture: a simple colony-forming assay identifies samples with the greatest potential to propagate and differentiate. *Br J Haematol* 107, 275-281 (1999).
11. Shi, S., et al. Bone formation by human postnatal bone marrow stromal stem cells is enhanced by telomerase expression. *Nat Biotechnol* 20, 587-591 (2002).
12. Simonsen, J. L., et al. Telomerase expression extends the proliferative life-span and maintains the osteogenic potential of human bone marrow stromal cells. *Nat Biotechnol* 20, 592-596 (2002).
13. Boland, G. M., Perkins, G., Hall, D. J. & Tuan, R. S. Wnt 3a promotes proliferation and suppresses osteogenic differentiation of adult human mesenchymal stem cells. *J Cell Biochem* 93, 1210-1230 (2004).
14. Martin, I., Muraglia, A., Campanile, G., Cancedda, R. & Quarto, R. Fibroblast growth factor-2 supports ex vivo expansion and maintenance of osteogenic precursors from human bone marrow. *Endocrinology* 138, 4456-4462 (1997).
15. Solchaga, L. A., et al. FGF-2 enhances the mitotic and chondrogenic potentials of human adult bone marrow-derived mesenchymal stem cells. *J Cell Physiol* 203, 398-409 (2005).
16. Tamama, K., Fan, V. H., Griffith, L. G., Blair, H. C. & Wells, A. Epidermal growth factor as a candidate for ex vivo expansion of bone marrow-derived mesenchymal stem cells. *Stem Cells* 24, 686-695 (2006).
17. Tsutsumi, S., et al. Retention of multilineage differentiation potential of mesenchymal cells during proliferation in response to FGF. *Biochem Biophys Res Commun* 288, 413-419 (2001).
18. Walsh, S., et al. Expression of the developmental markers STRO-1 and alkaline phosphatase in cultures of human marrow stromal cells: regulation by fibroblast growth factor (FGF)-2 and relationship to the expression of FGF receptors 1-4. *Bone* 27, 185-195 (2000).
19. Catelas, I., et al. Human mesenchymal stem cell proliferation and osteogenic differentiation in fibrin gels in vitro. *Tissue Eng* 12, 2385-2396 (2006).
20. Matsubara, T., et al. A new technique to expand human mesenchymal stem cells using basement membrane extracellular matrix. *Biochem Biophys Res Commun* 313, 503-508 (2004).
21. Mauney, J. R., et al. Matrix-mediated retention of in vitro osteogenic differentiation potential and in vivo bone-forming capacity by human adult bone marrow-derived mesenchymal stem cells during ex vivo expansion. *J Biomed Mater Res A* 79, 464-475 (2006).
22. Burns, J. S., et al. Tumorigenic heterogeneity in cancer stem cells evolved from long-term cultures of telomerase-immortalized human mesenchymal stem cells. *Cancer Res* 65, 3126-3135 (2005).
23. Brickman, Y. G., et al. Structural modification of fibroblast growth factor-binding heparan sulfate at a determinative stage of neural development. *J Biol Chem* 273, 4350-4359 (1998).
24. Guimond, S. E. & Turnbull, J. E. Fibroblast growth factor receptor signalling is dictated by specific heparan sulphate saccharides. *Curr Biol* 9, 1343-1346 (1999).
25. Kang, H. B., et al. Basic fibroblast growth factor activates ERK and induces c-fos in human embryonic stem cell line MizhES1. *Stem Cells Dev* 14, 395-401 (2005).

26. Nurcombe, V., Ford, M. D., Wildschut, J. A. & Bartlett, P. F. Developmental regulation of neural response to FGF-1 and FGF-2 by heparan sulfate proteoglycan. *Science* 260, 103-106 (1993).
27. Friedenstein, A. J., Chailakhjan, R. K. & Lalykina, K. S. The development of fibroblast colonies in monolayer cultures of guinea-pig bone marrow and spleen cells. *Cell Tissue Kinet* 3, 393-403 (1970).
28. Gronthos, S. & Simmons, P. J. The growth factor requirements of STRO-1-positive human bone marrow stromal precursors under serum-deprived conditions in vitro. *Blood* 85, 929-940 (1995).
29. Alter, O., Brown, P. O. & Botstein, D. Singular value decomposition for genome-wide expression data processing and modeling. *Proc Natl Acad Sci USA* 97, 10101-10106 (2000).
30. Holter, N. S., et al. Fundamental patterns underlying gene expression profiles: simplicity from complexity. *Proc Natl Acad Sci USA* 97, 8409-8414 (2000).
31. Bild, A. H., et al. Oncogenic pathway signatures in human cancers as a guide to targeted therapies. *Nature* 439, 353-357 (2006).
32. Pomeroy, S. L., et al. Prediction of central nervous system embryonal tumour outcome based on gene expression. *Nature* 415, 436-442 (2002).
33. Cawthon, R. M. Telomere measurement by quantitative PCR. *Nucleic Acids Res* 30, e47 (2002).
34. Guillot, P. V., Gotherstrom, C., Chan, J., Kurata, H. & Fisk, N. M. Human first-trimester fetal MSC express pluripotency markers and grow faster and have longer telomeres than adult MSC. *Stem Cells* 25, 646-654 (2007).
35. Aggarwal S. Pittenger MF. Human mesenchymal stem cells modulate allogeneic immune cell responses. *Blood* 2005; 105: 1815-22.
36. Bartholomew A. et al. Mesenchymal stem cells suppress lymphocyte proliferation in vitro and prolong skin graft survival in vivo. Exp Hematol 2002; 30: 42-8.
37. Lange C. et al. Accelerated and Safe Expansion of Human Mesenchymal Stromal Cells in Animal Serum-Free Medium for Transplantation and Regenerative Medicine. *J Cell Physiol.* 2007 October; 213(1):18-26.
38. Li, W-J., Tuli R., Huang X, Laquerriere P. and Tuan R S. Multilineage differentiation of human mesenchymal stem cells in a three-dimensional nanofibrous scaffold. *Biomaterials* 26, 5158-5166 (2005).
39. Cleveland, W. S. Robust locally weighted regression and smoothing scatterplots. *J. Amer. Stat. Assoc.* 74, 829-836 (1979).
40. Raychaudhuri, S., Stuart, J. M. & Altman, R. B. Principal components analysis to summarize microarray experiments: application to sporulation time series. *Pac. Symp. Biocomput.* 455-66 (2000).
41. Peres-Neto, P. R., Jackson, D. A. & Somers, K. M. Giving meaningful interpretation to ordination axes: Assessing loading significance in principal component analysis. *Ecology.* 84(9), 2347-2363 (2003).
42. Ghosh, D. Resampling methods for variance estimation of singular value decomposition analyses from microarray experiments. *Funct. Integr. Genomics.* 2(3), 92-7 (2002).
43. Kerr, K. & Churchill, G. A. Bootstrapping cluster analysis: Assessing the reliability of conclusions from microarray experiments. *Proc. Natl. Acad. Sci. USA.* 98(16), 8961-8966 (2001).
44. Tseng, G. C. & Wong, W. W. Tight clustering: A resampling-based approach for identifying stable and tight patterns in data. *Biometrics.* 61(1), 10-6 (2005).
45. Efron, B. & Tibshirani, R. J. An Introduction to the Bootstrap. (Chapman and Hall, New York 1993).
46. Besse, P. & De Falguerolles, A. In Computer Intensive Methods in Statistics (eds Hardle, W. & Simar, L.) 167-176 (Springer, New York, 1993).
47. Efron, B. & Tibshirani, R. J. In Advances in Biometry: 50 years of the International Biometric Society (eds Armitage, P. & David, H. A.) 131-149 (Wiley, New York, 1996).

---

The invention claimed is:

1. An in vitro method for expanding a population of stromal precursor antigen-1$^{+bright}$ (STRO-1$^{+bright}$) cells, the method comprising:
   (a) in vitro culturing a human mesenchymal stem cells population with heparan sulfate 2 (HS2)-containing media under conditions and for a time sufficient for proliferation of STRO-1$^{+bright}$ cells, wherein such STRO-1$^{+bright}$ cells are mesenchymal precursor cells capable of giving rise to colony forming units-fibroblastic (CFU-Fs); and
   (b) collecting STRO-1$^{+bright}$ cells, wherein the STRO-1$^{+bright}$ cells are increased in expansion in the HS2-containing media relative to expansion of the STRO-1$^{+bright}$ cells in the absence of HS2.

* * * * *

SEQUENCE LISTING

```
<160> NUMBER OF SEQ ID NOS: 21

<210> SEQ ID NO 1
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 1
ttcgaggccc tgtaattgga                                              20

<210> SEQ ID NO 2
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 2
gcagcaactt taatatacgc tattgg                                       26

<210> SEQ ID NO 3
<211> LENGTH: 18
<212> TYPE: DNA
<213> ORGANISM: Artificial sequence
```

```
<220> FEATURE:
<223> OTHER INFORMATION: Synthetic sequence: Probe

<400> SEQUENCE: 3
agtccacttt aaatcctt                                                 18

<210> SEQ ID NO 4
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 4
atgccctgga gcttcagaag                                               20

<210> SEQ ID NO 5
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 5
tggtggagct gacccttgag                                               20

<210> SEQ ID NO 6
<211> LENGTH: 21
<212> TYPE: DNA
<213> ORGANISM: Artificial sequence
<220> FEATURE:
<223> OTHER INFORMATION: Synthetic sequence: Probe

<400> SEQUENCE: 6
acgttggcta agaatgtcat c                                             21

<210> SEQ ID NO 7
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 7
agaggaagca atcaccaaaa tga                                           23

<210> SEQ ID NO 8
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 8
ttgagaaagc acaggccatt c                                             21

<210> SEQ ID NO 9
<211> LENGTH: 20
<212> TYPE: DNA
<213> ORGANISM: Artificial sequence
<220> FEATURE:
<223> OTHER INFORMATION: Synthetic sequence: Probe

<400> SEQUENCE: 9
ctgctttaat tttgctcagc                                               20
```

```
<210> SEQ ID NO 10
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 10
ggaaagtcaa gagcaccata acct                                              24

<210> SEQ ID NO 11
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 11
ttccaccacc agtttatcat cct                                               23

<210> SEQ ID NO 12
<211> LENGTH: 21
<212> TYPE: DNA
<213> ORGANISM: Artificial sequence
<220> FEATURE:
<223> OTHER INFORMATION: Synthetic sequence: Probe

<400> SEQUENCE: 12
aaatcaacca ccataaagag a                                                 21

<210> SEQ ID NO 13
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 13
gagggaccgg agttatgaca ag                                                22

<210> SEQ ID NO 14
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 14
ggcacagagg ccagatacaa g                                                 21

<210> SEQ ID NO 15
<211> LENGTH: 23
<212> TYPE: DNA
<213> ORGANISM: Artificial sequence
<220> FEATURE:
<223> OTHER INFORMATION: Synthetic sequence: Probe

<400> SEQUENCE: 15
aatattttgc tttatcagcc gat                                               23

<210> SEQ ID NO 16
<211> LENGTH: 28
<212> TYPE: DNA
<213> ORGANISM: Artificial sequence
<220> FEATURE:
<223> OTHER INFORMATION: Synthetic sequence: Primer
```

-continued

```
<400> SEQUENCE: 16
gtactttcca atctcagtca ctctagga                                              28

<210> SEQ ID NO 17
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 17
ttttattttg cagtctgccc agtt                                                  24

<210> SEQ ID NO 18
<211> LENGTH: 19
<212> TYPE: DNA
<213> ORGANISM: Artificial sequence
<220> FEATURE:
<223> OTHER INFORMATION: Synthetic sequence: Probe

<400> SEQUENCE: 18
cccctctctt tctaagaga                                                        19

<210> SEQ ID NO 19
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 19
aaaggcaact cgtacccaaa ttt                                                   23

<210> SEQ ID NO 20
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 20
agtgggtaat gcgcttggat                                                       20

<210> SEQ ID NO 21
<211> LENGTH: 18
<212> TYPE: DNA
<213> ORGANISM: Artificial sequence
<220> FEATURE:
<223> OTHER INFORMATION: Synthetic sequence: Probe

<400> SEQUENCE: 21
caagacacaa acatgacc                                                         18
```